(12) United States Patent
Parish et al.

(10) Patent No.: US 12,239,650 B2
(45) Date of Patent: Mar. 4, 2025

(54) COMPOUNDS FOR TREATING AND PREVENTING NET ASSOCIATED COMPLICATIONS

(71) Applicants: The Australian National University, Acton (AU); Griffith University, Nathan (AU)

(72) Inventors: Christopher Parish, Kingston (AU); Connor O'Meara, Newcastle (AU); Lucy Coupland, Chifley (AU); Benjamin Ju Chye Quah, Jerrabomberra (AU); Farzaneh Kordbacheh, Belconnen (AU); Anna Orlov, Narrabundah (AU); Anna Browne, Acton (AU); Ross Stephens, Stirling (AU); Gregory David Tredwell, Turner (AU); Lee Andrew Philip, Greenleigh (AU); Karen Knox, Ellen Grove (AU); Laurence Mark von Itzstein, Gilston (AU); Chih-Wei Chang, Upper Commera (AU); Anne Bruestle, Acton (AU); David Anak Simon Davis, Belconnen (AU)

(73) Assignees: The Australian National University, Acton (AU); Griffith University, Nathan (AU)

( * ) Notice: Subject to any disclaimer, the term of this patent is extended or adjusted under 35 U.S.C. 154(b) by 752 days.

(21) Appl. No.: 17/430,756

(22) PCT Filed: Feb. 25, 2019

(86) PCT No.: PCT/AU2019/050156
§ 371 (c)(1),
(2) Date: Aug. 13, 2021

(87) PCT Pub. No.: WO2020/172698
PCT Pub. Date: Sep. 3, 2020

(65) Prior Publication Data
US 2022/0168327 A1 Jun. 2, 2022

(51) Int. Cl.
*A61K 31/7028* (2006.01)
*A61K 31/7016* (2006.01)
*A61P 37/06* (2006.01)

(52) U.S. Cl.
CPC ...... *A61K 31/7028* (2013.01); *A61K 31/7016* (2013.01); *A61P 37/06* (2018.01)

(58) Field of Classification Search
CPC .............. A61K 31/7016; A61K 31/702; A61K 31/7028; A61P 29/00; A61P 37/00
See application file for complete search history.

(56) References Cited

U.S. PATENT DOCUMENTS 9,226,939 B2 * 1/2016 Stephens ................. A61P 31/10

FOREIGN PATENT DOCUMENTS

EP 0771815 A1 5/1997
WO 1994022885 A1 10/1994
(Continued)

OTHER PUBLICATIONS

Liu (The British Journal of Surgery, 2017, 104(9), pp. 1215-1225).*
(Continued)

*Primary Examiner* — Pancham Bakshi
(74) *Attorney, Agent, or Firm* — Greenberg Traurig, LLP; David J. Dykeman; Natalie Salem

(57) ABSTRACT

The present invention relates to compounds with high chemical stability and methods for inhibiting the pathological activity of NETs in a subject. In particular, the invention relates to compounds with high chemical stability, uses thereof and methods for inhibiting or ameliorating NET mediated ailments (such as, for example, sepsis, systemic immune response syndrome (SIRS) and ischemia reperfusion injury (IRI)). More particularly, the invention relates to methods and uses of a polyanionic sulfated cellobioside modified with a small uncharged glycosidically linked substituent at its reducing terminus, wherein the presence of the substituent results in a molecule with high chemical stability without affecting the ability of the molecule to be effective in the therapy of NET mediated ailments. For example, the
(Continued)

present invention relates to methods and uses of β-O-methyl cellobioside sulfate (mCBS) or a pharmaceutically acceptable salt thereof (e.g., mCBS.Na), in the therapy of a range of NET mediated ailments in subjects.

6 Claims, 9 Drawing Sheets

(56) References Cited

FOREIGN PATENT DOCUMENTS

| | | | |
|---|---|---|---|
| WO | 2005061523 A1 | 7/2005 |
| WO | 2005085264 A1 | 9/2005 |
| WO | 2012071611 A1 | 6/2012 |
| WO | 2019113645 A1 | 6/2019 |

OTHER PUBLICATIONS

Probst, K.C., et al., "Synthesis and Conformational Investigations of Sulfated Carbohydrates", Journal of Carbohydrate Chemistry, 2001, vol. 20, Issue 7-8, pp. 549-560.
Silk, E., et al., "The role of extracellular histone in organ injury", Cell Death and Disease, 2017, vol. 8, e2812.
International Search Report and Written Opinion in PCT International Application No. PCT/AU2019/050156 mailed Apr. 29, 2019.
International Preliminary Report on Patentability in PCT International Application No. PCT/AU2019/050156 mailed Mar. 16, 2021.

* cited by examiner

COMPOUNDS FOR TREATING AND PREVENTING NET ASSOCIATED COMPLICATIONS

RELATED APPLICATIONS

This application is a U.S. national phase application of PCT International Patent Application No. PCT/AU2019/050156, filed on Feb. 25, 2019, the disclosure of which is incorporated herein by reference in its entirety.

TECHNICAL FIELD

The present invention relates to compounds and methods for inhibiting the pathological activity of neutrophil extracellular traps (NETs) in a subject. In particular, the invention relates to compounds, uses and methods for inhibiting or ameliorating NET mediated ailments (such as, for example, sepsis, systemic immune response syndrome (SIRS) and ischemia reperfusion injury (IRI)). More particularly, the invention relates to methods and uses of a polyanionic sulfated cellobioside. Preferably, the polyanionic sulfated cellobioside is modified with a small uncharged glycosidically linked substituent at its reducing terminus, wherein the presence of the substituent results in a molecule with high chemical stability without affecting the ability of the molecule to be effective in the therapy of NET mediated ailments. For example, the present invention relates to methods and uses of cellobioside sulfate (CBS), β-O-methyl cellobioside sulfate (mCBS) or a pharmaceutically acceptable salt thereof, in the therapy of a range of NET mediated ailments in subjects.

BACKGROUND

Neutrophils are innate immune granulocytes (most abundant white blood cells) that have a central role in pathogen clearance, immune regulation and disease pathology. They eliminate infectious agents by mechanisms such as phagocytosis, reactive oxygen species' (ROS) generation and the release of microbicidal molecules from neutrophilic granules (degranulation).

Neutrophils also extrude a meshwork of chromatin fibres that are decorated with granule-derived antimicrobial peptides and enzymes such as neutrophil elastase (NE), cathepsin G, and myeloperoxidase (MPO). These extruded structures are called neutrophil extracellular traps (NETs).

A purpose for NETs is to disarm pathogens using their high local concentration of antimicrobial components. As such, NETs represent an important strategy to immobilize and kill invading organisms. NET scaffolds consist of web-like chromatin fibres with a diameter of 15-17 nm; DNA and histones represent the major NET constituents.

In addition to their antimicrobial properties, NETs serve as a physical barrier that prevents spread of pathogens and potentially injurious proteins. For example, absorption of granule proteins into NETs can keep potentially injurious proteins, like proteases, from diffusing away from an injury where they can induce damage in tissue adjacent to a site of inflammation.

NET formation and release is thought to arise in two possible situations:
 a. NETosis, a distinct form of active cell death that is characterized by release of decondensed chromatin and granular contents to the extracellular space. During NETosis, nuclear and granular membranes dissolve, and nuclear contents decondense into the cytoplasm. This is followed by plasma membrane rupture and release of chromatin decorated with granular proteins into the extracellular space;
 b. a DNA/serine protease extrusion mechanism from intact neutrophils, where mitochondrial DNA release is apparently not associated with cell death.

NETosis is largely induced in response to microbial cues and endogenous danger signals, including proinflammatory cytokines (TNF-α, IL-8), platelets, activated endothelial cells (ECs), nitric oxide, monosodium urate crystals, and various autoantibodies. Ordinarily, this process is tightly regulated to prevent excessive tissue damage during acute inflammation or chronic inflammatory and autoimmune disease.

Although NET formation is integral to the innate immune response providing a beneficial strategy for combatting disease, NETs also figure prominently at the centre of various infectious and non-infectious pathologic states such as hypoxia or sterile inflammation. In this respect, NETs because of their construct and nature are putative sources of molecules with immune effector and proinflammatory roles that, in susceptible individuals, can promote a range of infectious and non-infectious diseases, inflammation, tissue damage and autoimmunity. When they form in excessive amounts NETs can be injurious to the endothelium and underlying tissue. Such injury often results from NET degradation by both endogenous and microbial-derived nucleases. When NETs degrade, they release histones that are cytotoxic for not only microbes but also for host epithelial and endothelial cells.

NETs have been directly implicated in a range of medical conditions including or associated with, for example and only by way of illustration: hyper-inflammatory responses to infection (including, bacterial, viral and parasitic), during sepsis, preeclampsia, colon mucosa of patients with the inflammatory bowel disease ulcerative colitis and associated with the production of IgG antinuclear double stranded DNA antibodies in children infected with *P. falciparum* (malaria); fibrosis where functional parenchymal organ tissue is replaced by fibrotic tissue, which can severely diminish organ function, transfusion-related acute lung injury, deep vein thrombosis and cancer.

Despite the clinical use of modern antibiotics, there remains a significant level of morbidity and mortality due to ineffective treatment of NET related ailments. Accordingly, there is an urgent need for drugs that neutralise the damaging effects of excessive levels of NETs, without impeding the beneficial effects of neutrophils.

To date there exists a dearth of compounds that present a treatment for NET induced ailments. It is against this background and the growing recognition of the role of NETs in multiple diseases that the present invention has been developed.

SUMMARY OF INVENTION

The present invention is predicated on the finding that certain anti-NET polyanionic compounds, as described herein, interact electrostatically with NETs in the circulation of animals to neutralise the cytopathic properties of NETs. Complexing of such polyanionic molecules with NETs in the circulation of a living animal provides a means to at least ameliorate the cytotoxic activity of NETs.

In particular, the inventors have identified that certain sulfated disaccharides are effective at neutralizing the pathological effects of NETs. For example, a polyanionic sulfated cellobioside modified with a small uncharged glycosidically linked substituent at its reducing terminus provides a chemically stable polyanion that is able to provide highly effective treatment for NET associated complication (such as, for example, sepsis, SIRS and IRI and at least ameliorate those conditions in patients).

Use of a sulfated cellobioside modified with a small uncharged substituent at its reducing terminus, with resultant chemical stability, presents or provides a new general principal of application in the field of treating patients suffering from NET associated complications and/or preventing NET associated complications from occurring in at risk patients.

In a first aspect of the invention, there is provided a compound for use in the treatment or prevention of at least a NET associated complication in a subject, wherein the compound comprises: a polyanionic sulfated cellobioside or a polyanionic sulfated cellobioside modified with a small uncharged glycosidically linked substituent at its reducing terminus or a pharmaceutically acceptable salt thereof.

Preferably, where the polyanionic sulfated cellobioside is modified it desirably posseses a small uncharged glycosidically linked substituent at the reducing terminus of the polyanionic sulfated cellobioside. This preferably improves the chemically stability of the polyanion, relative to the same polyanion that is sulfated at its reducing terminus.

Compounds of the invention when present in a therapeutically or pharmaceutically effective amount provide a means for ameliorating, treating or preventing NET associated complications.

In an embodiment of the invention, the modified polyanionic sulfated cellobioside, has the general structure:

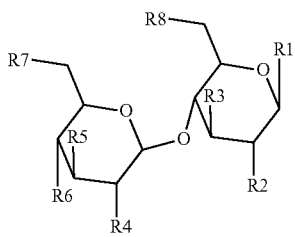

wherein:
R1 is a sulfate group or a small uncharged glycosidically linked substituent, for example, O or S—($C_{1-6}$)alkyl; and
R2 to R8 are each selected from: (i) a small uncharged O-linked substituent or (ii) a sulfate group.

Preferably, R1 is O or S—($C_{1-6}$)alkyl. When R1 is O or S—($C_{1-6}$)alkyl, the substituent preferably improves the chemically stability of the polyanion, compared to the same polyanion with a sulfate group at R1.

Preferably, R2 to R8 are each selected from: (a) an unmodified hydroxyl group; or (b) a sulfate group.

More preferably, R1 is a methoxy or ethoxy group and R2 to R8 are each a sulfate group.

Desirably, the class of compound has a high net negative charge, i.e. it is a polyanion.

The anomeric configuration of the small uncharged glycoside substituent (R1) can be in either of the α or β position. Preferably, the small uncharged substituent is in the β configuration.

In a highly-preferred form of the invention, the compound is CBS, mCBS or a pharmaceutically acceptable salt thereof, wherein when the compound is mCBS it is desirably a sulfated β-O-methyl cellobioside disaccharide. By way of illustration, when the compound is mCBS it is desirably the sodium salt of β-O-Methyl Cellobioside Sulfate, viz Sodium β-O-Methyl Cellobioside Sulfate (mCBS.Na).

mCBS is preferred as it is a highly stable relative to CBS and well tolerated at high concentrations.

In a second aspect of the invention, there is provided a method for treating (either therapeutically or preventively) a medical condition, ailment or disease involving NETs in a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

In a third aspect of the invention, there is provided a method for ameliorating NET accumulation in a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

In an embodiment of the second or third aspect of the invention the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

For example, in an embodiment of the second or third aspect of the invention, the method is used to treat or prevent a condition or ailment associated with an NET associated complication such as, for example, sepsis, SIRS or IRI.

In certain exemplary embodiments according to the second or third aspects of the invention, the identified methods can further comprise the step of: administering to the subject, together with or concomitantly with the modified sulfated cellobioside, a therapeutically or pharmaceutically effective amount of a second active agent, compound or composition selected from: one or more of anti-inflammatory agents, antibiotic agents, antiviral agents, antifungal agents and/or any other form of pharmaceutical composition that treats one or more condition that a subject is afflicted with or at risk of being afflicted with.

According to this embodiment, the second active agent, compound or composition provides an adjunct treatment to the treatment directed to the NET associated complication (such as, for example, sepsis, SIRS or IRI) and/or for medical conditions or diseases associated with such complications. Preferably, the second active agent, compound or composition comprises one or more of anti-inflammatory agents.

Preferably, the second active agent presents a means for medical intervention of a disease that a patient is afflicted with that is related to or distinct from the medical ailment treated by the compounds of this invention, said second active agent providing an adjunct treatment for the patient.

In a fourth aspect of the invention, there is provided a method for treating or preventing a medical condition or disease associated with NET cytotoxicity in a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

In an embodiment of the fourth aspect of the invention the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

In one preferred example of the fourth aspect of the invention, the method is used to neutralise NETs that (i) are cytotoxic towards the endothelium in a subject and/or (ii) contribute to endothelial dysfunction in a subject.

In addition, or alternatively, the method is used to treat a septic or SIRS condition or an IRI or a disease associated with sepsis, SIRS or an IRI that is, caused by or mediated by a release of NETs in a subject following infection, inflammation or hypoxia or any infection, inflammatory or hypoxia response in a subject.

In a fifth aspect of the invention, there is provided a therapeutic or pharmaceutical composition for use in treating an NET associated complication comprising: at least a polyanionic sulfated cellobioside or a polyanionic sulfated cellobioside modified with a small uncharged glycosidically linked substituent at its reducing terminus or a pharmaceutically acceptable salt thereof.

In an embodiment of the fifth aspect of the invention the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Preferably, the compound is present in a therapeutically or pharmaceutically effective amount in the therapeutic or pharmaceutical composition. The composition can also include a therapeutically or pharmaceutically acceptable carrier, excipient and/or diluent. The compound in the therapeutic or pharmaceutic is either in a neutral free base form or salt form. Preferably, the polyanionic sulfated cellobioside compound is mCBS or more particularly is the sodium salt of β-O-Methyl Cellobioside Sulfate.

In certain exemplary embodiments, according to the fifth aspect of the invention, the identified composition can also comprise a second active agent, compound or composition selected from: one or more of anti-inflammatory agents, antibiotic agents, antiviral agents, antifungal agents and/or any other form of therapeutic or pharmaceutical compound that treats one or more conditions that the subject is afflicted with.

According to this embodiment, the second active agent, compound or composition desirably provides an adjunct therapy for sepsis, SIRS or an IRI or for a medical condition or disease associated with sepsis, SIRS or an IRI. Preferably, the second active agent, compound or composition comprises one or more of anti-inflammatory agents.

In a sixth aspect of the invention, there is provided a use of a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof, in the manufacture of a medicament for treating a medical condition, ailment or disease involving NETs.

In an embodiment of the sixth aspect of the invention the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

For example, in an embodiment of the sixth aspect of the invention, there is provided a use of a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof, in the manufacture of a medicament for the treatment or prevention of sepsis, SIRS or an IRI or a medical condition or disease associated with sepsis, SIRS or an IRI in a subject. Preferably, the modified sulfated cellobioside is mCBS or more particularly is a pharmaceutically acceptable salt thereof such as mCBS.Na.

In one embodiment of such use, the medicament is for the treatment of sepsis, or SIRS or a medical condition or disease associated with sepsis or SIRS in a subject, wherein said treatment ameliorates or inhibits said sepsis or SIRS or said condition or disease associated with said sepsis or SIRS.

In another embodiment of such use, the medicament is for the treatment of an IRI or of a medical condition or disease associated with an IRI in a subject, wherein said treatment ameliorates or inhibits said IRI or said condition or disease associated with said injury.

In yet another embodiment of such use, the medicament is used to neutralise NETs that (i) are cytotoxic towards the endothelium in a subject, or (ii) contribute to endothelial dysfunction in a subject, or (iii) initiate coagulation by activating platelets in a subject, or (iv) induce red cell fragility and resultant anaemia in a subject.

In yet another embodiment, the manufactured medicament may also include a therapeutic or pharmaceutically effective amount of a second active agent, compound or composition. According to this embodiment, the second active agent, compound or composition provides an adjunct therapy for treating a medical condition, ailment or disease involving NETs. Desirably, the second active agent, compound or composition provides an adjunct therapy for the treatment of sepsis, SIRS or an IRI or for a medical condition or disease associated with sepsis, SIRS or an IRI. Preferably, the second active agent is selected from: one or more of anti-inflammatory agents, antibiotic agents, antiviral agents, antifungal agents and/or any other form of therapeutic or pharmaceutical compound that treats one or more conditions that the subject is afflicted with. More preferably, the second active agent, compound or composition comprises one or more of anti-inflammatory agents.

When the modified sulfated cellobioside compound is used in any of the methods of the invention the compound can be administered or formulated for administration to the subject in need thereof, in a single dose of formulation. In certain alternative embodiments, the modified sulfated cellobioside compound is administered, or formulated for administration to the subject in need thereof, as a multi-dose formulation.

Additional objectives, advantages and novel features will be set forth in the description which follows or will become apparent to those skilled in the art upon examination of the drawings and the ensuing detailed description of several non-limiting embodiments which follows.

BRIEF DESCRIPTION OF THE DRAWINGS

The disclosure will provide details in the following description of preferred embodiments with reference to the following figures wherein.

DETAILED DESCRIPTION OF THE PREFERRED EMBODIMENTS

Figure 1:
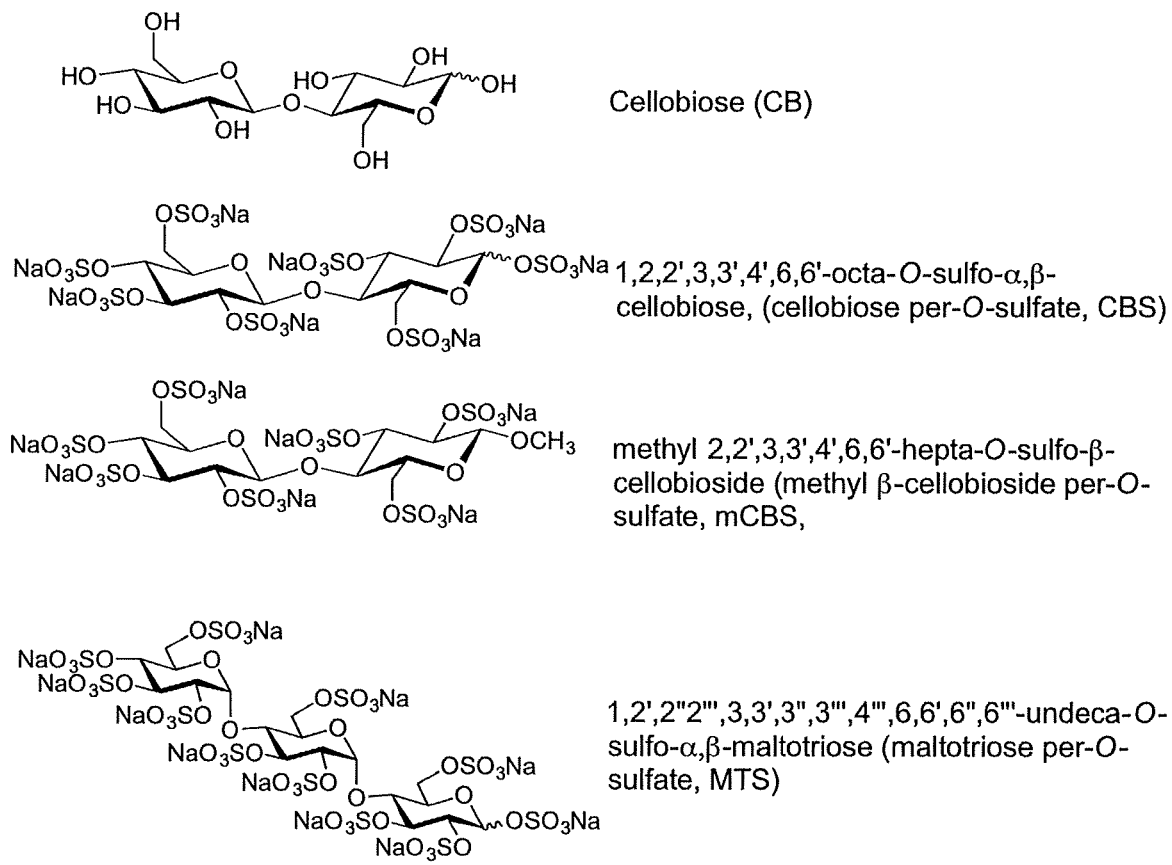
FIG. 1 Chemical structures of compounds selected.

The present invention is directed to the use of modified sulfated cellobioside compounds, that have high chemical stability, in the treatment or prevention of NET mediated ailments (such as, for example, sepsis, SIRS or IRI) in a subject. Such compounds can ameliorate or inhibit or prevent the cytotoxic effect of NETs in a subject.

For convenience, the following sections generally outline the various meanings of terms used herein. Following this discussion, general exemplary embodiments illustrating the invention are disclosed, followed by specific examples providing more specific illustration of properties of various exemplary embodiments of the invention.

General

Those skilled in the art will appreciate that the invention described herein is susceptible to variations and modifications other than those specifically described without departing from the spirit and scope of the invention as herein described. The invention includes all such variations and modifications. The invention also includes all the steps, features, compositions and components, referred to or indicated in the specification, individually or collectively, and any and all combinations or any two or more of said steps or features. Functionally equivalent products, compositions of matter and methods are clearly within the scope of the invention as described herein.

All publications, references, documents, patents and patent applications cited in the herein, whether supra or infra, are hereby incorporated herein by reference in their entirety, which means that those publications, references, documents, patents and patent applications should be read and considered as part of this text. That any publication, reference, document, patent and patent application cited in this text is not repeated in this text is merely for reasons of conciseness. However, publications, references, documents, patents and patent applications mentioned herein are cited for describing and disclosing the protocols, reagents and products that which are reported in the publications and which might be used in connection with the invention. Nothing herein is to be construed as an admission that the invention is not entitled to antedate such disclosure by virtue of prior invention or for any other reason. All statements as to the date or representation as to the contents of these documents is based on the information available to the applicants and does not constitute any admission as to the correctness of the dates or contents of these documents.

Any manufacturer's instructions, descriptions, product specifications, and product sheets for any products mentioned herein or in any document incorporated by reference herein, are hereby incorporated herein by reference, and may be employed in the practice of the invention.

Definitions for selected terms used herein may be found within the summary of invention and the detailed description of the invention and apply throughout. Unless otherwise defined, all other scientific and technical terms used herein have the same meaning as commonly understood to one of ordinary skill in the art to which the invention belongs. If there is an apparent discrepancy between the usage of a term in the art and its definition provided herein, the definition provided within the specification shall prevail.

Definitions

Other than in the operating examples, or where otherwise indicated, all numbers expressing quantities of ingredients or reaction conditions used herein should be understood as modified in all instances by the term "about." For example, the term "about" when used in connection with percentages can mean±10%.

Unless the context requires otherwise, or the specification specifically states to the contrary, integers, steps, or elements of the invention recited herein as singular integers, steps or elements clearly encompass both singular and plural forms of the recited integers, steps or elements. Throughout this specification, unless stated otherwise or the context requires otherwise, reference to a single step, composition or matter, group of steps or group of compositions of matter shall be taken to encompass one and a plurality (i.e., one or more) or those steps, compositions or matter, group of steps or group of compositions of matter. Accordingly, as used herein and in the appended claims, the singular forms "a, "an" and "the" include plural references unless the context clearly dictates otherwise. Thus, for example, reference to "a sulfated cellobioside modified with a small uncharged substituent at its reducing terminus or a pharmaceutically acceptable salt thereof" includes a plurality of such modified sulfated cellobioside compounds or a plurality of salts thereof, and so forth.

Throughout the specification and claims, unless the context requires otherwise, the word "comprise" or variations such as "comprises" or "comprising", will be understood to imply the inclusion of a stated step or element or integer or group of steps or elements or integers but not the exclusion of any other step or element or integer or group of steps or elements or integers.

As used herein, the term "including", as well as variations such as "includes" and "included", will also be understood to be not limiting.

In this application, the use of "or" means "and/or" unless stated otherwise.

The invention described herein may include one or more range of values (for example, size, displacement and field strength etc.). A range of values will be understood to include all values within the range, including the values defining the range, and values adjacent to the range that lead to the same or substantially the same outcome as the values immediately adjacent to that value which defines the boundary to the range. For example, a person skilled in the relevant field will understand that a 10% variation in upper or lower limits of a range can be totally appropriate and is encompassed by the invention. More particularly, the variation in upper or lower limits of a range will be 5% or as is commonly recognised in the art, whichever is greater.

As used herein, the term "NET" refers to extracellular complexes of nucleosomes and proteins, e.g. proteins having anti-microbial activity. The nucleosomes may be derived from neutrophils, mast cells, eosinophils, monocytes, or leukocytes.

As used herein, the phrase "NET associated complication" means, without particular limitation, NET associated:
 a. systemic inflammatory responses to: infection (including bacteria, virus, fungal, parasitic infections), sepsis (including bacteria, virus, fungal, parasite, prion induced sepsis); or to non-infectious inducers including non-infectious Systemic inflammatory response syndrome surgery, trauma, haemorrhage, burns, acute pancreatitis, preeclampsia and acute kidney injury;
 b. hypoxia at the localised tissue level e.g. following blockage of an artery due to atherosclerosis, spontaneous rupture of a vessel, traumatic damage to a vessel and including cardiac and transplantation associated IRI; or at the whole body level following cessation of breathing e.g. due to drowning, gas exposure or cardiorespiratory arrest and includes ailments such as, for example, acute respiratory distress syndrome, ventilator-associated lung injury, chronic obstructive pulmonary disease and drug-mediated tissue injury;
c. haemostasis or vascular obstruction such as, for example, cardiovascular disease or chronic cardiovascular disease, such as atherosclerosis, coagulation and thrombosis (e.g., deep vein thrombosis); Transfusion-related acute lung injury (TRALI);
d. fibrosis where functional parenchymal organ tissue is replaced by fibrotic tissue, which can severely diminish organ function such as pulmonary fibrosis, idiopathic pulmonary fibrosi;
e. autoimmune disease states and inflammation disease states such as, for example, multiple sclerosis, tumour associated inflammation, hyper-inflammatory disease states, systemic lupus erythematosus, spondyloarthropathy, ankylosing spondylitis, psoriatic arthritis, reactive arthritis, enteropathic arthritis, inflammatory bowel disease, ulcerative colitis, cystic fibrosis (CF), Asthma, glomerulonephritis, chronic lung disease, Crohn's disease, irritable bowel disease, rheumatoid arthritis, juvenile rheumatoid arthritis, anti-neutrophil cytoplasmic antibody (ANCA) associated vasculitis (AAV) such as granulomatosis with polyangiitis, eosinophilic granulomatosis with polyangiitis and microscopic polyangiitis), characterized by destruction and inflammation of small vessels, familial Mediterranean fever, amyotrophic lateral sclerosis, Cancer, Sjogren's syndrome, early arthritis, viral arthritis, psoriasis, age-related organ fibrosis, idiopathic pulmonary fibrosis, juvenile diabetes (Type I), diabetes mellitus (Type 2), antiphospholipid syndrome,
f. various central nervous system diseases such as Huntington's disease
g. cytokine and chemokine induced degradation such as Gout.

The above cited conditions are associated with increased NETosis, and thus NETs can be targeted for treatment of these disorders.

As used herein, the terms "ailment", "condition" or "disease" (used interchangeably) means a medical complication associated with the release of NETs.

As used herein, the term "sepsis" includes within its meaning all stages of a sepsis disease or condition as characterised by standard medical reference texts and/or known to one of skill in the art. For example, sepsis includes severe sepsis, acute and chronic sepsis and septic shock. The term "sepsis" as used herein also includes episodes associated with infection. The term 'SIRS' (systemic immune response syndrome) used herein includes episodes not associated with infection such as, for example, trauma, burns, pancreatitis, organ transplantation, surgery, tumour lysis following therapeutic regimes for cancer, perinatal complications and immunosuppressive prophylaxis for allogeneic grafts.

As used herein, the terms "medical condition associated with sepsis or SIRS" or "disease associated with sepsis or SIRS" include within their meaning all signs and symptoms directly or indirectly associated with, derived from, caused by or accompanying any or all stages of sepsis or SIRS diseases or conditions as characterised by standard medical reference texts and/or known to one of skill in the art. For example, the medical conditions or diseases associated with sepsis or SIRS include one or more of the following signs or symptoms associated with, derived from, caused by or accompanying any or all stages of sepsis or SIRS diseases or conditions in a subject which may be manifested in the subject with or without infection: arterial hypotension, metabolic acidosis, decreased systemic vascular resistance, increased heart rate (tachycardia), increased breathing rate (tachypnoea), general or systemic inflammation, elevated or decreased white blood cell count (leucocytosis or leucopenia), increased NETs in blood, organ dysfunction such as acute organ dysfunction, dysfunction of the circulatory system, multiple organ dysfunction syndrome, disseminated intravascular coagulation (DIC), deposition of fibrin in the microvasculature of one or more organs, fever, confusion, pneumonia, cough with pneumonia, kidney infection, painful urination with a kidney infection, and/or septic shock.

As used herein, the terms "decrease", "reduced", "reduction", "decrease" or "inhibit" are all used generally to mean a decrease by a statistically significant amount. However, for avoidance of doubt, "reduced", "reduction" or "decrease" or "inhibit" means a decrease by at least 10% as compared to a reference level, e.g., in the absence of an agent, for example a decrease by at least about 20%, or at least about 30%, or at least about 40%, or at least about 50%, or at least about 60%, or at least about 70%, or at least about 80%.

As used herein, the terms "improve", "increased", 'increase" or "enhance" or "activate" are all used to generally mean an increase by a statically significant amount; for the avoidance of any doubt, the terms "improve", "increased", "increase" or "enhance" or "activate" means an increase of at least 10% as compared to a reference level, e.g., in in the absence of an agent, for example an increase of at least about 20%, or at least about 30%, or at least about 40%, or at least about 50%), or at least about 60%, or at least about 70%, or at least about 80%, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "administer", "administered" and "administering" refers to the placement of a composition into a subject by a method or route which results in at least partial localization of the composition at a desired site such that a desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration. In certain embodiments, the compound is a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside, improves the chemically stability of the polyanion, relative to the same polyanion that is sulfated at its reducing terminus. When the above compound is present in a composition such as a therapeutic or a therapeutic composition it will be prepared for parenteral administration, or another other method allowing delivery to a target site. Some exemplary modes of administration include, but are not limited to, injection, infusion, instillation, inhalation, or ingestion.

As used herein, the term "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

As used herein, the terms "treat," "treatment," "treating" and the like, in the context of the present invention insofar as it relates to any of the conditions or diseases recited herein means to relieve, alleviate, ameliorate, inhibit, slow down, reverse, or stop the progression, aggravation, deterioration, progression, anticipated progression or severity of at least one symptom or complication associated with such condition or disease. In an embodiment, the symptoms of a condition or disease are alleviated by at least 5%, at least 10%, at least 20%, at least 30%, at least 40%, or at least 50%.

As used herein, the phrases "effective amount" "therapeutically effective amount" or "effective dose" (used interchangeably herein) include within their meaning a sufficient but non-toxic amount of a compound or composition of the invention to provide a desired effect. The exact amount of a compound or composition required will vary from subject to subject depending on factors such as the desired effect, the species being treated, the age and general condition of the subject, the severity of the condition being treated, the agent being administered, the mode of administration, and so forth. Thus, it is not possible to specify an exact "effective amount". However, for any given case, an appropriate effective amount (dose) may be determined by one of ordinary skill in the art using only routine experimentation. Generally, a therapeutically effective amount can vary with the subject's history, age, condition, sex, as well as the severity and type of the medical condition in the subject, and administration of other pharmaceutically active agents.

As used herein, reference to use of a compound or composition in therapeutic or pharmaceutical applications will be understood to be equally applicable to human and non-human, such as veterinary, applications. Hence, it will be understood that, except where otherwise indicated, reference to a "patient", "subject" or "individual" (used interchangeably herein) means a human or non-human, such as an individual of any species of social, economic or research importance including but not limited to, mammalian, avian, lagomorph, ovine, bovine, equine, porcine, feline, canine, primate and rodent species. More preferably, the patient, subject or individual is an animal belonging to a mammalian species. The mammalian species is desirably a human or non-human primate or a companion animal such as a domesticated dog, cat, horse, monkey, mouse, rat, rabbit, sheep, goat, cow or pig. In one particularly preferred example, the patient, subject or individual is a human.

Definitions for selected terms used herein may be found within the detailed description of the invention and apply throughout. Unless otherwise defined, all other scientific and technical terms used herein have the same meaning as commonly understood to one of ordinary skill in the art to which the invention belongs.

Illustrative Embodiments of the Invention

The ensuing detailed description of this invention is included solely for the purposes of illustrating the invention and should not be understood in any way as a restriction on the broad description of the invention, as set out above.

1. Compounds of the Invention

In a first aspect of the invention, there is provided a compound for use in the treatment of a NET mediated complication wherein the compound comprises: a polyanionic sulfated cellobioside or a polyanionic sulfated cellobioside modified with a small uncharged glycosidically linked substituent at its reducing terminus or a pharmaceutically acceptable salt thereof. The substituent rendering the molecule high chemical stability, relative to the same polyanion but which is sulfated at its reducing terminus. Preferably, this class of compound should have a high net negative charge.

Compounds of the invention can ameliorate NET mediated complications (such as sepsis or ischemia reperfusion injuries) both preventatively i.e. as a prophylactic pretreatment to a medical procedure or therapeutically during treatment after the conditions or disease has occurred.

In an embodiment of the invention, the modified polyanionic sulfated cellobioside, has the general structure:

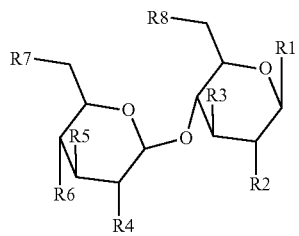

wherein:
R1 is a sulfate group or a small uncharged glycosidically linked substituent, for example, O or S—($C_{1-6}$)alkyl; and
R2 to R8 are each selected from: (i) a small uncharged O-linked substituent or (ii) a sulfate group.

Preferably, R1 is O or S—($C_{1-6}$)alkyl. When R1 is O or S—($C_{1-6}$)alkyl, the selected substituent preferably improves the chemically stability of the polyanion, compared to the same polyanion with a sulfate group at R1.

Preferably, R2 to R8 are each selected from: (a) an unmodified hydroxyl group; or (b) a sulfate group.

More preferably, R1 is a methoxy or ethoxy group and R2 to R8 are each a sulfate group.

Desirably, the class of compound has a high net negative charge, i.e. it is a polyanion.

The anomeric configuration of the small uncharged glycoside substituent (R1) can be in either of the α or β position. Preferably, the small uncharged substituent is in the β configuration.

In a highly-preferred form of the invention, the compound is β-O-Methyl Cellobioside Sulfate or a pharmaceutically acceptable salt thereof, which is a sulfated β-O-methyl cellobioside disaccharide. By way of illustration, the compound is the sodium salt of β-O-Methyl Cellobioside Sulfate.

mCBS is highly stable relative to CBS and well tolerated at high doses.

The small uncharged glycosidically linked substituent that is present at the reducing terminus of the polyanionic sulfated cellobioside, improves the chemically stability of the polyanion relative to the same polyanion that is sulfated at its reducing terminus.

Chemical stability as used herein represents the tendency of the compound of the invention to resist change (in particular decomposition in its natural environment or when exposed to air, heat, light, pressure, or other natural conditions, or due to internal reaction.

A compound of the invention is "stable" if it is does not significantly decompose, relative to the same polyanion that is sulfated at its reducing terminus, after at least one-month storage under conditions of anticipated use or normal environmental conditions.

A compound of the invention will have decomposed significantly if it has lost 3 or more sulfate groups after at least one-month storage, under conditions of anticipated use or normal environmental conditions. Preferably, a compound of the invention will have decomposed significantly if it has lost 2 sulfate groups after at least one-month storage, under conditions of anticipated use or normal environmental conditions. Most preferably, a compound of the invention will have decomposed significantly if it has lost 1 sulfate group after at least one-month storage, under conditions of anticipated use or normal environmental conditions.

Preferably, the compound of the invention is chemically stable for at least 2, 3, 4, 5, 6, 7, 8, 9, 10, 11, 12, 13, 14, 15, 16, 17, 18, 19, 20, 21, 22, 23 or 24 months when stored in a phosphate formulation buffered to pH 7.5 and stored at 2-8° C. More preferably, stability is measured over a period of 6 months to 2 years with the compound being stored in a phosphate formulation buffered to pH 7.5 and stored at about 2-8° C.

As used herein, the phrase "pharmaceutically acceptable salt(s)" includes those salts which, within the scope of sound medical judgement, are suitable for use in contact with tissues of humans and lower animals without the undue toxicity, irritation, allergic response and the like, and are commensurate with a reasonable benefit/risk ratio.

Pharmaceutically acceptable salts are well known in the art. They include, for example, acid addition salts (formed with the free amino groups of the protein) derived from inorganic acids (e.g., hydrochloric or phosphoric acids, or from organic acids (e.g., citric, acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

In a preferred form of the invention the modified sulfated cellobioside of the invention, is present as a pharmaceutically acceptable salt. By way of illustration, the compound is the sodium salt of β-O-Methyl Cellobioside Sulfate, viz Sodium β-O-Methyl Cellobioside Sulfate (mCBS.Na).

Modified sulfated cellobioside compounds or pharmaceutically acceptable salts thereof used in the methods or compositions of the present invention may be prepared by methods known to those skilled in the art. For example, methods for preparing sulfated compounds modified with an uncharged substituent at its reducing termini are generally described in Katrin C Probst and Hans Peter Wessel, 2001, *J. Carbohydrate Chemistry*, 20 (7 & 8): 549-560, which is incorporated herein by reference in its entirety.

2. Treatment Methods

As compounds of the invention and therapeutic or pharmaceutical compositions including said compounds can ameliorate or prevent the pathological activity of NETs, the present invention provides as a second aspect of the invention, a method of treatment or prevention for NET associated complications, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

Further, in a third aspect of the invention, there is provided a method for ameliorating NET accumulation in a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

In an embodiment of the second and third aspects of the invention the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

The present invention as described by the second and third aspects of the invention contemplates treating ameliorating or preventing a variety of different NET ailments that are caused by the formation of NETs and the resulting toxicity therefrom. According to these aspects of the invention, the respective methods can be used for the treatment or prevention of NET associated complications in a subject.

Typically NET associated conditions are attributable to increased NETosis, and thus NETs can be targeted for treatment of these disorders by modifying (preferably reducing) the level or the activity of the NETs to a basal concentration or quantity that is consistent with their normal pathophylsiological levels in a subject.

The largest group of NET activators are pathogenic Gram-positive and Gram-negative bacteria lipoteichoic acid and LPS, and breakdown products of prokaryotic proteins. Some examples of bacteria that induce NETs include, by way of illustration: *S. aureus, Streptococcus* sp., *P. aeruginosa, Bordetella pertussis, Mannheimia haemolytica, Aggregatibacter actinomycetemcomitans, Neisseria gonorhoeae, Neisseria meningitidis, Yersinia enterocolitica, Vibrio cholerae, Leptospira species, H. influenzae, K. pneumoniae, L. monocytogenes, M. tuberculosis,* and *S. flexneri*). Net Activation also arises from: fungal infection (examples include, by way of illustration: (*Aspergillus* spp. such as, *A. nidulans, A. fumigatus* and *Candida* spp. such as *C. albicans*); protozoan parasite infection (examples include, by way of illustration: *L. amazonensis* or its surface lipophosphoglycan, *Strongyloides stercoralis, Eimeria bovis, Leishmania* species, *Toxoplasma gondii, Plasmodium falciparum*); or viral infection (examples include, by way of illustration: HIV/SIV, Hantaan virus Respiratory Syncytial Virus (RSV), influenza virus). These pathogenis activators are presented only by way of example and do not constitute a defined list of organisms that represent NET activators. Those skilled in the field will be aware of the NET activation ability of an organism.

The response caused by infection with organisms such as those listed above is generally an inflammatory response causing activation of inflammation pathways, however other responses such as autimmune responses, lung diseases, thrombosis or other microbial activity may also be present as a result of NET activation. Net activation also arises from non-infectious inducers including non-infectious systemic inflammatory response syndrome, surgery, trauma, haemorrhage, burns and kidney injury; hypoxia at the localised tissue level or at the whole body level; haemostasis or vascular obstruction; fibrosis where functional parenchymal organ tissue is replaced by fibrotic tissue; autoimmune disease states and inflammation disease, various central nervous system diseases as well as cytokine and chemokine induced degradation.

In an embodiment of the second or third aspects of the invention, the respective methods may further comprise administering to the subject, at the same time or concomitantly with the compound of the invention, a second therapeutic agent (such as anti-inflammatory agents, antibiotic agents, antiviral agents, antifungal agents or other forms of medical intervention) that is distinct from the compound of the invention that provides an adjunct treatment for a medical condition that the subject is or may suffer from.

Preferably, as an example of these aspects of the invention, the respective methods provide a means for treating or preventing sepsis or SIRS or a medical condition or disease associated with sepsis or SIRS in a subject.

As another example of these aspects of the invention the respective methods provide a means for treating or preventing IRI or a medical condition or disease associated with IRI in a subject.

Preferably, the method ameliorates the condition or a disease state sufficiently to allow a physician to administer other drugs to treat secondary conditions. Thus, the invention also includes administering a therapeutically effective amount of a polyanionic sulfated cellobioside modified with a small uncharged glycosidically linked substituent at its reducing terminus or a pharmaceutically acceptable salt thereof to a subject, for the purposes of ameliorating NET associated complications in the patient.

In certain exemplary embodiments according to the second or third aspects of the invention, the identified methods can further comprise the step of: administering to the subject, together with or concomitantly with the modified sulfated cellobioside, a therapeutically or pharmaceutically effective amount of a second active agent, compound or composition selected from: one or more of anti-inflammatory agents, antibiotic agents, antiviral agents, antifungal agents and/or any other form of pharmaceutical composition that treats one or more condition that a subject is afflicted with or at risk of being afflicted with.

According to this embodiment, the second active agent, compound or composition provides an adjunct treatment to the treatment directed to the NET associated complication (such as, for example, sepsis, SIRS or IRI) and/or for medical conditions or diseases associated with such complications. Preferably, the second active agent, compound or composition comprises one or more of anti-inflammatory agents.

Preferably, the second active agent presents a means for medical intervention of a disease that a patient is afflicted with that is related to or distinct from the medical ailment treated by the compounds of this invention, said second active agent providing an adjunct treatment for the patient.

Therapeutics and/or pharmaceutical compositions of the invention disclosed herein may be administered either therapeutically or preventively. In a therapeutic application, compounds and compositions are administered to a patient already suffering from NET associated complications or an ailment associated with NET associated complications, in an amount sufficient to cure or at least partially arrest its symptoms. The compound or composition should be provided in a quantity of the active compound sufficient to effectively treat the patient either in a single dose or as part of a treatment regime e.g., a multi-dose treatment regime. In a preventative application, compounds and compositions of the invention are administered to a subject at risk of developing an ailment associated with NET associated complications, in an amount sufficient to at least partially arrest the ailment's symptoms and/or complications.

In a fourth aspect of the invention, there is provided a method for treating or preventing a medical condition, ailment or disease associated with NET mediated pathology in a subject, wherein the method comprises the step of: administering to the subject a therapeutically or pharmaceutically effective amount of: a polyanionic sulfated cellobioside or a polyanionic sulfated cellobioside modified with a small uncharged glycosidically linked substituent at its reducing terminus or a pharmaceutically acceptable salt thereof.

In an embodiment of the fourth aspects of the invention the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

In one preferred example, the method is used to treat NETs that (i) are cytotoxic towards the endothelium in a subject, or (ii) contribute to endothelial dysfunction in a subject, or (iii) initiate coagulation by activating platelets in a subject, or (iv) induce red cell fragility and resultant anaemia in a subject.

Patients suffering from an infection of the type caused by one or more of the above identified organisms have increased levels of NETs present in their blood.

In an embodiment of the second, third or fourth aspects of the invention, there is provided a method of treating (either prophylactically or therapeutically) NET associated sepsis in a subject by inhibiting the cytotoxic activity of NETs, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemically stability of the polyanion relative to the same polyanion that is sulfated at its reducing terminus. More preferably, the modified sulfated cellobioside is mCBS or more particularly is a pharmaceutically acceptable salt thereof such as mCBS.Na.

As demonstrated herein, compounds of the invention in particular mCBS block the toxic effects of NETs and thereby are useful as a treatment for sepsis.

Thus, compounds of the invention and therapeutic or pharmaceutical compositions including said compounds provide a means for ameliorating the cytotoxic activity of NET proteins in sepsis, including both pre-treatment (in the case of a medical procedure) and treatment after sepsis has occurred.

In a highly preferred exemplary form of the invention, according to any aspect, embodiment or example describes herein, the compound of the invention is used to treat or prevent one or more of the following discussed ailments or conditions.

A. Sepsis

Sepsis (including septic shock) is a systemic reaction to infection characterized by arterial hypotension, metabolic acidosis, decreased systemic vascular resistance, tachypnoea and organ dysfunction. Sepsis (including septic shock) is also a systemic inflammatory response to infection associated with and mediated by the activation of a number of host defence mechanisms including the cytokine network, leukocytes, and the complement and coagulation fibrinolysis systems. Disseminated intravascular coagulation (DIC) with widespread deposition of fibrin in the microvasculature of various organs may be an early manifestation of sepsis. DIC is an important mediator in the development of the multiple organ failure syndrome and contributes to the poor prognosis of patients with septic shock.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Symptoms of sepsis are often related to an underlying infectious process and if left untreated can manifest as severe sepsis (sepsis with acute organ dysfunction) or septic shock (sepsis with refractory arterial hypotension). When two or more of the systemic inflammatory response syndrome criteria (e.g., general inflammation, fever, elevated white blood cell count (leukocytosis), and raised heart rate (tachycardia) and breathing rate (tachypnoea)) are met without evidence of infection, patients may be diagnosed simply with "SIRS", which is a septic inflammatory state affecting the whole body.

Many patients with sepsis exhibit a rapid decline over a 24-48 hour period. Rapid treatment is essential for effective sepsis treatment. Unfortunately, diagnosis of type of infection requires microbiological analysis to identify the pathogen which may take several days. Therefore, therapy to eliminate a pathogen (e.g. antibiotic therapy) must be initiated without knowledge of the type and species of the pathogen, and with no means of knowing the extent of the infection. The present invention provides such a method.

Patients suffering from sepsis have increased levels of NETs present in their blood. NETs have been implicated as important mediators of sepsis pathology.

In an embodiment of the second, third or fourth aspects of the invention, there is provided a method of treating (either prophylactically or therapeutically) NET associated sepsis in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

As demonstrated herein, compounds of the invention in particular mCBS block the toxic effects of NETs and thereby are useful as a treatment for sepsis.

Thus, compounds of the invention and therapeutic or pharmaceutical compositions including said compounds provide a means for ameliorating the cytotoxic activity of NETs in sepsis, including both pre-treatment (in the case of a medical procedure) and treatment after sepsis has occurred.

B. Non-Infectious SIRS

Non-infectious Systemic inflammatory response syndrome (SIRS) is an inflammatory state affecting the whole body. It is the body's response to non-infectious insult. Although the definition of SIRS refers to it as an "inflammatory" response, it actually has pro- and anti-inflammatory components.

SIRS is a serious condition related to systemic inflammation, organ dysfunction, and organ failure. It is a subset of cytokine storm, in which there is abnormal regulation of various cytokines. SIRS is also closely related to sepsis, in which patients satisfy criteria for SIRS and have a suspected or proven infection. Causes of non-infection SIRS include, for example: trauma, from surgery, traumatic haemorrhage, burns and acute pancreatitis, by way of illustration.

In an embodiment of the second, third or fourth aspects of the invention, there is provided a method of treating (either prophylactically or therapeutically) NET associated non-infectious SIRS in a subject by inhibiting the cytotoxic activity of NETs, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

As demonstrated herein, compounds of the invention in particular mCBS block the toxic effects of NETs and thereby are useful as a treatment for non-infectious SIRS.

Thus, compounds of the invention and therapeutic or pharmaceutical compositions including said compounds provide a means for ameliorating the cytotoxic activity of NETs in non-infectious SIRS, including both pre-treatment (in the case of a medical procedure) and treatment after non-infectious SIRS has occurred.

B.1 Trauma

Physical trauma is a serious and body-altering physical injury, such as the crushing or amputation of a limb.

Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to SIRS, but also significantly increase the risk of subsequent infection and sepsis.

NETs are released following trauma or severe cellular stress in the absence of infection. Patients suffering from trauma can have increased levels of NETs present in their blood. NETs have been implicated as important mediators of trauma pathology.

In an embodiment of the second, third or fourth aspects of the invention, there is provided a method of treating (either prophylactically or therapeutically) NET associated trauma in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in trauma patients.

Thus, compounds of the invention and therapeutic or pharmaceutical compositions including said compounds provide a means for ameliorating the cytotoxic activity of NETs in trauma, including both pre-treatment (in the case of a medical procedure) and treatment after trauma injury has occurred.

B.2. Surgery

Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

In an embodiment of the second, third or fourth aspects of the invention, there is provided a method of treating (either prophylactically or therapeutically) NET associated surgical trauma in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

As a rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anaesthesia, antiseptic conditions, typical surgical instruments, and suturing or stapling. All forms of surgery are considered invasive procedures; so-called non-invasive surgery usually refers to an excision that does not penetrate the structure being addressed (e.g., laser ablation of the cornea) or to a radio-surgical procedure (e.g., irradiation of a tumour).

As compounds of the invention and therapeutic or pharmaceutical compositions including said compounds, can ameliorate the cytotoxic activity of NETs, the present invention provides a treatment for use in surgical trauma, including both pre-treatment (in the case of a medical procedure) and treatment after surgical injury has occurred.

B.3. Traumatic Haemorrhage

Traumatic haemorrhage accounts for much of the wide-ranging international impact of injury, causing a large proportion of deaths and creating great morbidity in the injured. Despite differences in pre-hospital care, the acute management of traumatic haemorrhage is similar around the world and follows well accepted published guidelines. A critically injured patient's care occurs as four, often overlapping segments: the resuscitative, operative, and critical care phases. The diagnosis and control of bleeding should be a high priority during all the phases of trauma care and is especially important in the patient who is in haemorrhagic shock. Early attempts at haemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of haemorrhage, and appropriate transfusion of blood and blood products are provided. In the operative phase, surgical control of the haemorrhage and any other injury, and additional transfusion is provided. Finally, the critical care phase provides for post-operative support and tissue perfusion).

As compounds of the invention and therapeutic or pharmaceutical compositions including said compounds, can ameliorate the cytotoxic activity of NETs, the present invention provides to treatment for use in traumatic haemorrhage, including both pre-treatment (in the case of a medical procedure) and treatment after traumatic haemorrhage has occurred.

B.4. Burns

A burn can be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

Various burns lead to an increase in the levels of NETs which in turn are associated with toxicity. To the extent that the NETs toxicity is present, the present invention seeks to reduce this toxicity using the pharmaceutical compositions of the present invention, thereby reducing or alleviating discomfort on the part of the patient, as well as permitting higher doses of the therapy.

Patients suffering from burns can have increased levels of NETs present in their blood. NETs have been implicated as important mediators of burns pathology.

In an embodiment of the second or third aspect of the invention, there is provided a method of ameliorating NET induced cytotoxicity caused by burns to a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in burns patients.

Thus, compounds of the invention and therapeutic or pharmaceutical compositions including said compounds provide a means for ameliorating the cytotoxic activity of NETs in a burn in a subject.

B.5. Acute Pancreatitis

Acute pancreatitis is characterized as rapidly-onset inflammation of the pancreas by sterile inflammation and acinar cell death, including necrosis and apoptosis.

Depending on its severity, acute pancreatitis can have severe complications and high mortality despite treatment. While mild cases are often successfully treated with conservative measures or laparoscopy, severe cases require invasive surgery (often more than one intervention) to contain the disease process.

Patients suffering from acute pancreatitis can have increased levels of NETs present in their blood. NETS have been implicated as important mediators of acute pancreatitis pathology.

In an embodiment of the second, third or fourth aspects of the invention, there is provided a method of treating (either prophylactically or therapeutically) NET associated acute pancreatitis in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in acute pancreatitis patients.

Thus, compounds of the invention and therapeutic or pharmaceutical compositions including said compounds provide a means for ameliorating the cytotoxic activity of NET.s in acute pancreatitis, including both pre-treatment (in the case of a medical procedure) and treatment after acute pancreatitis has occurred.

C. Ischemia-Reperfusion Injury

Ischemia reperfusion injuries (including transplantation associated Ischemia reperfusion injuries) and drug-mediated tissue injury result in sterile inflammation, a process occurring in the absence of microorganisms.

Ischemia is a restriction in blood supply to tissues, causing a shortage of oxygen that is needed for cellular metabolism. In prolonged ischemia (60 min or more), hypoxanthine is formed as a breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signalling.

Reperfusion injury refers to damage due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane can in turn cause the release of more free radicals. Such reactive species act indirectly in redox signalling to turn on apoptosis. Leukocytes also build up in small capillaries, obstructing them and leading to more ischemia.

Reperfusion injury also plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

NET levels are elevated in animal Ischemia reperfusion models with liver, kidney, lung, and brain injury, suggesting an important role of NETs in the regulation of sterile inflammation.

NETs mediate not only liver, but also acute kidney injury or ischemic stroke through direct toxicity or pro-inflammatory effects. Inhibition of NET formation and activity presents a therapeutic strategy for tissue injury.

Patients suffering from ischemia reperfusion injuries (including transplantation associated ischemia reperfusion injuries) and drug-mediated tissue injury have increased levels of NETs present in their blood. NETs have been implicated as important mediators of ischemia/reperfusion and drug-mediated tissue injury pathology.

In an embodiment of the second, third or fourth aspects of the invention, there is provided a method of treating (either prophylactically or therapeutically) NET associated IRI and/or drug-mediated tissue injury in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in ischemia/reperfusion and drug-mediated tissue injury patients.

Thus, compounds of the invention and therapeutic or pharmaceutical compositions including said compounds provide a means for ameliorating the cytotoxic activity of NETs in ischemia/reperfusion and drug-mediated tissue injury, including both pre-treatment (in the case of a medical procedure) and treatment after ischemia/reperfusion and drug-mediated tissue injury has occurred.

D. Coagulation and Thrombosis

Coagulation is the biological process by which blood forms clots. A precise regulation mechanism prevents aberrant coagulation that results in an increased risk of bleeding (haemorrhage) or obstructive clotting (thrombosis).

Patients suffering from coagulation and or thrombosis can have increased levels of NETs present in their blood. NETs have been implicated as important mediators of coagulation and or thrombosis pathology.

In an embodiment of the second or third aspect of the invention, there is provided a method of treating coagulation and or thrombosis in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in coagulation and or thrombosis patients.

Thus, compounds of the invention and therapeutic or pharmaceutical compositions including said compounds provide a means for ameliorating the cytotoxic activity of NETs in coagulation and or thrombosis, including both pre-treatment (in the case of a medical procedure) and treatment after coagulation or thrombosis has occurred.

E. Autoimmune/Inflammatory Disease

The present invention contemplates the treatment of a variety of autoimmune and/or inflammatory disease states such as multiple sclerosis, spondyloarthropathy, ankylosing spondylitis, psoriatic arthritis, reactive arthritis, enteropathic arthritis, ulcerative colitis, Crohn's disease, irritable bowel disease, rheumatoid arthritis, juvenile rheumatoid arthritis, familial Mediterranean fever, amyotrophic lateral sclerosis, Sjogren's syndrome, early arthritis, viral arthritis, or psoriasis. The diagnosis and treatment of these diseases are well documented in the literature.

Patients suffering from autoimmune and/or inflammatory disease have increased levels of NETs present in their blood. NETs have been implicated as important mediators of autoimmune and/or inflammatory disease pathology.

In an embodiment of the second or third aspect of the invention, there is provided a method of treating autoimmune and/or inflammatory disease in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in autoimmune and/or inflammatory disease patients.

Thus, compounds of the invention and therapeutic or pharmaceutical compositions including said compounds provide a means for ameliorating the cytotoxic activity of NETs in autoimmune and/or inflammatory disease, including both pre-treatment (in the case of a medical procedure) and treatment after autoimmune and/or inflammatory disease has occurred.

F. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary oedema.

ARDS is caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI) including transfusion-related acute lung injury (TRALI).

ARDS can occur within 24 to 48 hours of an injury or attack of acute illness. In such a case the patient usually presents with shortness of breath, tachypnoea, and symptoms related to the underlying cause, i.e., shock. Long term illnesses can also trigger it, such as malaria. The ARDS may then occur sometime after the onset of a particularly acute case of the infection.

Patients suffering from ARDS can have increased levels of NETs present in their blood. NETs have been implicated as important mediators of ARDS pathology.

In an embodiment of the second, third or fourth aspects of the invention, there is provided a method of treating (either prophylactically or therapeutically) NET associated acute respiratory distress syndrome in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in ARDS patients.

Thus, compounds of the invention and therapeutic or pharmaceutical compositions including said compounds provide a means for ameliorating the cytotoxic activity of NETs in ARDS, including both pre-treatment (in the case of a medical procedure) and treatment after ARDS has occurred.

G. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments.

Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

Patients suffering from NET associated cardiovascular disease have increased levels of NETs present in their blood, which have been implicated as important mediators of NET associated cardiovascular disease pathology.

In an embodiment of the second, third or fourth aspects of the invention, there is provided a method of treating (either prophylactically or therapeutically) NET associated cardiovascular disease in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in NET associated cardiovascular disease patients.

Thus, compounds of the invention and therapeutic or pharmaceutical compositions including said compounds provide a means for ameliorating the cytotoxic activity of NET proteins in NET associated cardiovascular disease, including both pre-treatment (in the case of a medical procedure) and treatment after NET associated cardiovascular disease has occurred.

H. Fibrosis

Patients suffering from fibrosis have increased levels of NETs present in their blood. NETs have been implicated as important mediators of fibrosis pathology.

In an embodiment of the second or third aspect of the invention, there is provided a method of ameliorating NET induced cytotoxicity caused fibrosis in a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in fibrosis patients.

Thus, compounds of the invention and therapeutic or pharmaceutical compositions including said compounds provide a means for ameliorating the cytotoxic activity of NETs in fibrosis in a subject, including both pre-treatment (in the case of a medical procedure) and treatment after fibrosis has occurred.

I. Diabetes

Patients suffering from diabetes can have increased levels of NETs present in their blood. NETs have been implicated as important mediators of diabetes pathology.

The invention provides methods for treating NET associated complications in diabetes (e.g inflammation and delayed wound healing). The methods comprise administering a therapeutically effective amount of at least one compound of the invention to a subject diagnosed with Type 1, Type 1.5 or Type 2 diabetes.

In an embodiment of the second or third aspect of the invention, there is provided a method of ameliorating diabetes in a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in diabetes patients.

In certain embodiments, the symptom of diabetes having NET involvement is inflammation. Reduction in inflammation can be monitored by physical examination, as well as the reduction in the presence of inflammatory markers.

In certain embodiments, a method for treatment of diabetes is provided, that comprises the administration of a therapeutically effective amount of an agent used to treat diabetes and at least one compound of the invention. The agent used to treat diabetes can be insulin or another agents selected from the following Biguanides, Metformin (Glucophage), Metformin liquid (Riomet), Metformin extended release (Glucophage XR, Fortamet, Glumetza), Sulfonylureas, Glimepiride (Amaryl), Glyburide (Diabeta, Micronase), Glipizide (Glucotrol, Glucotrol XL), Micronized glyburide (Glynase), Meglitinides, Repaglinide (Prandin), D-Phenylalanine Derivatives, Nateglinide (Starlix), Thiazolidinediones, Pioglitazone (TZDs), Pioglitazone, (Actos), DPP-4 Inhibitor, Sitagliptin (Januvia), Saxagliptin (Onglyza), Linagliptin (Tradjenta), Alpha-glucosidase, Acarbose (Precose), Miglitol (Glyset), Bile Acid Sequestrants, Colesevelam (Welchol), Pioglitazone & metformin (Actoplus Met), Glyburide & metformin (Glucovance), Glipizide & metformin (Metaglip), Sitagliptin & metformin (Janumet), Saxagliptin & metformin (kombiglyze), Repaglinide & metformin (Prandimet) and Pioglitazone & glimepiride (Duetact).

Thus, compounds of the invention and therapeutic or pharmaceutical compositions including said compounds provide a means for ameliorating the cytotoxic activity of NETs in diabetes in a subject. As such the present invention provides a treatment for diabetes in a subject, including both pre-treatment (in the case of a medical procedure) and treatment after diabetes has occurred.

J. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the actions of NETs, the present invention seeks to reduce this toxicity using the pharmaceutical compositions of the present invention, thereby reducing or alleviating discomfort on the part of the patient, as well as permitting higher doses of the therapy.

Patients suffering from the side effects of various forms of cancer therapy, including chemotherapy, radiation, and cytokine therapy can have increased levels of NETs present in their blood. NETs have been implicated as important mediators of these side effects.

In an embodiment of the second or third aspect of the invention, there is provided a method of ameliorating the side effects of various forms of cancer therapy, including chemotherapy, radiation, and cytokine therapy in a subject by inhibiting the cytotoxic activity of NETs, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment for the side effects of various forms of cancer therapy, including chemotherapy, radiation, and cytokine therapy.

In a highly preferred form of the invention the compound used in treating the side effects of various forms of cancer therapy, including chemotherapy, radiation, and cytokine therapy in the patients undergoing such therapy is the compound β-O-Methyl Cellobioside Sulphate or a pharmaceutically acceptable salt thereof. For example, the compound used in the method is Sodium β-O-Methyl Cellobioside Sulphate.

Thus, compounds of the invention and therapeutic or pharmaceutical compositions including said compounds provide a means for ameliorating the cytotoxic activity of NETs in the side effects of various forms of cancer therapy, including chemotherapy, radiation, and cytokine therapy, including both pre-treatment (in the case of a medical procedure) and treatment after these therapies have occurred.

K. Wound Healing

Also provided are methods for use in wound healing. As used herein "wound healing" refers to the intricate process where the skin (or another organ-tissue) repairs itself after injury. The classic model of wound healing is divided into three or four sequential, yet overlapping, phases: (1) haemostasis, when clot stops bleeding, (2) inflammation, (3) proliferation and (4) remodelling. Upon injury to the skin, a set of complex biochemical events takes place in a closely orchestrated cascade to repair the damage. During the inflammation phase, bacteria and cell debris are phagocytosed and removed from the wound by white blood cells. Platelet-derived growth factors (stored in the alpha granules of the platelets) are released into the wound that cause the migration and division of cells during the proliferative phase. The proliferation phase is characterized by angiogenesis, collagen deposition, granulation tissue formation, epithelialization, and wound contraction. New blood vessels are formed and fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue.

Patients suffering from wound healing difficulties can have increased levels of NETs present in their blood. NETs have been implicated as important mediators of wound healing pathology.

In an embodiment of the second or third aspect of the invention, there is provided a method of ameliorating NET induced cytotoxicity caused during wound healing in a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in patients suffering from wound healing difficulties.

Thus, compounds of the invention and therapeutic or pharmaceutical compositions including said compounds provide a means for ameliorating the cytotoxic activity of NETs in treating wounds in a subject.

L. Central Nervous System Disease

Patients suffering from central nervous system disease can have increased levels of NETs present in their blood. NETs have been implicated as important mediators of central nervous system disease pathology. For example, Huntington's disease is an autosomal dominant neurodegenerative disorder caused by a polyglutamine repeat expansion, resulting in an expanded polyglutamine track in the huntington protein.

In an embodiment of the second or third aspect of the invention, there is provided a method of ameliorating NET induced central nervous system disease in a subject, said method comprising the step of: administering to the subject a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof.

According to this embodiment the selected compound is preferably a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

Compounds such as mCBS can block the toxic effects of NETs and thereby are useful as a treatment in central nervous system disease.

Thus, compounds of the invention and therapeutic or pharmaceutical compositions including said compounds provide a means for ameliorating the cytotoxic activity of NETs in central nervous system disease in a subject, including both pre-treatment (in the case of a medical procedure) and treatment after central nervous system disease has occurred.

3. Therapeutic and Pharmaceutical Forms

In a fifth aspect of the invention, there is provided a therapeutic or pharmaceutical composition for use in treating an NET associated complication comprising: at least a polyanionic sulfated cellobioside modified with a small uncharged glycosidically linked substituent at its reducing terminus or a therapeutically or pharmaceutically acceptable salt thereof. Preferably, the composition includes a therapeutically or pharmaceutically acceptable carrier, excipient and/or diluent. The compound in the therapeutic or pharmaceutic may be in a neutral free base form or salt form. Preferably, the compound is the sodium salt of β-O-Methyl Cellobioside Sulfate.

As used here, the terms "pharmaceutically acceptable" or "therapeutically effective" refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Methods for preparing administrable compositions are apparent to those skilled in the art, and are described in more detail in, for example, Remington's Pharmaceutical Science, 15th ed., Mack Publishing Company, Easton, Pa., hereby incorporated by reference in its entirety.

As used here, the term "pharmaceutically-acceptable carrier" or "a pharmaceutically acceptable excipient" or "pharmaceutically acceptable diluent" "therapeutically-acceptable carrier" or "a therapeutically acceptable excipient" or "therapeutically acceptable diluent" means a material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier, diluent and excipient must be "acceptable" in the sense of being compatible with the other ingredients of the formulation and not injurious to the patient. It is a material that is not biologically or otherwise undesirable i.e., the material can be applied to an individual along with the active agent without causing unacceptable biological effects or interacting in a deleterious manner with any one or more of the components of the composition in which it is contained. Some examples of materials that can serve as pharmaceutically-acceptable carriers, diluents and excipients include, but are not limited to: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, binding agents, fillers, lubricants, colouring agents, disintegrants, release agents, coating agents, sweetening agents, flavouring agents, perfuming agents, preservative, water, salt solutions, alcohols, antioxidants, polyethylene glycols, gelatin, lactose, amylose, magnesium stearate, talc, silicic acid, viscous paraffin, hydroxymethylcellulose, polyvinylpyrrolidone and the like can also be present in the formulation. The terms such as "excipient", "carrier", "diluent" and "pharmaceutically acceptable carrier" or the like are used interchangeably herein.

Examples of therapeutically or pharmaceutically acceptable carriers, excipients or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, *arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethyl-cellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions described herein can additionally contain other adjunct components conventionally found in pharmaceutical compositions, at their art-established usage levels. Thus, for example, the compositions can contain additional, compatible, pharmaceutically-active materials such as, for example, antipruritics, astringents, local anaesthetics or anti-inflammatory agents. However, such materials, when added, should not unduly interfere with the biological activities of the components of the compositions described herein.

As described in detail below, the therapeutically or pharmaceutical acceptable compositions described herein can be specially formulated for administration in solid or liquid form, including those adapted for the following: (1) oral administration, for example, drenches (aqueous or nonaqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) injection directly into the organ needing treatment such as by intraparenchymal (into the brain), intrathecal, intraventricular or intrahepatic administration; (4) topical application, for example, as a cream, lotion, gel, ointment, or a controlled-release patch or spray applied to the skin; (5) in an aerosol form suitable for administration by inhalation, such as by intranasal inhalation or oral inhalation, (6) intravaginally or intrarectally, for example, as a pessary, cream, suppository or foam; (7) sublingually; (8) ocularly as an eye drop; (9) transdermally; (10) transmucosally; or (11) nasally.

In one embodiment, the composition of the invention is administered by injection such as by parenteral injection (such as by subcutaneous, intramuscular or intravenous injection) or locally to tissues and organs such as by intraparenchymal (into the brain), intrathecal, intraventricular or intrahepatic administration.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

Sterile injectable solutions can be prepared by incorporating the pharmaceutical composition of the invention in the required amount in an appropriate solvent with one or a combination of ingredients enumerated above, as required, followed by filtered sterilisation. By way of illustration, a single dose may be dissolved in 1 ml of isotonic NaCl solution and either added to 1000 ml of fluid or injected at the proposed site of infusion, (see for example, "Remington's Pharmaceutical Sciences" 15th Edition, pages 1035-1038 and 1570-1580).

In the case of injectable solutions, the carrier can be a solvent or dispersion medium containing, for example, water, Ringer's solution, isotonic saline, phosphate buffered saline, ethanol, polyol (for example, glycerol, propylene glycol (eg 1,2 propylene glycol), and liquid polyetheylene glycol, and the like), suitable mixtures thereof, and vegetable oils.

The proper fluidity can be maintained, for example, using a coating such as lecithin, by the maintenance of the required particle size in the case of dispersion and using surfactants. Prevention of the action of microorganisms can be achieved by including various anti-bacterial and or anti-fungal agents. Suitable agents are well known to those skilled in the art and include, for example, parabens, chlorobutanol, phenol, benzyl alcohol, ascorbic acid, thiomerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

In a second embodiment, the composition of the invention is administered orally, for example, with an inert diluent or an assimilable edible carrier. For oral therapeutic administration, the pharmaceutical composition may be incorporated with excipients and used in the form of ingestible tablets, buccal tablets, troches, capsules, elixirs, suspensions, syrups, wafers, and the like.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition, these oral formulations may contain suitable flavouring and colourings agents.

When used in capsule form the capsules may be coated with compounds such as glyceryl monostearate or glyceryl distearate which delay disintegration. Tablets, troches, pills, capsules and the like can also contain the following: a binder such as gum tragacanth, acacia, corn starch or gelatin; excipients such as dicalcium phosphate; an additional disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring.

When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both.

Liquid forms for oral administration (such as a syrup or elixir) can contain, in addition to the above agents, a liquid carrier, a sweetening agent (e.g. sucrose), a preservative (eg methyl and propylparabens), a dye and flavouring such as cherry or orange flavour. Suitable liquid carriers include water, oils such as olive oil, peanut oil, sesame oil, sunflower oil, safflower oil, *arachis* oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like. The emulsions for oral administration may further comprise one or more emulsifying agents. Suitable emulsifying agents include dispersing agents as exemplified above or natural gums such as guar gum, gum acacia or gum tragacanth.

In a third exemplary embodiment, the composition of the invention is administered directly to the airways of a subject in the form of an aerosol or by nebulization. For use as aerosols, solution or suspension of the pharmaceutical acceptable compositions of the invention can be packaged in a pressurized aerosol container together with suitable propellants, for example, hydrocarbon propellants like propane, butane, or isobutane with conventional adjuvants. Such compositions can also be administered in a non-pressurized form such as in a nebulizer or atomizer.

Aerosols for the delivery to the respiratory tract are known in the art: see, for example, Adjei, A. and Garren, *J. Pharm. Res.*, 1: 565-569 (1990); Zanen, P. and Lamm, J-W. J. *Int. J. Pharm.*, 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)).

In a fourth exemplary embodiment, the composition may be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which are incorporated herein by reference.

In addition, the therapeutic or pharmaceutical acceptable composition of the invention according to any aspect, embodiment or example described hereof, can be incorporated into sustained-release preparations and formulations. Such therapeutic or pharmaceutical compositions may further include a suitable buffer to minimise acid hydrolysis. Suitable buffer agent agents are well known to those skilled in the art and include, but are not limited to, phosphates, citrates, carbonates and mixtures thereof.

Compounds of the invention may also be administered in the form of a "prodrug". A prodrug is an inactive form of a compound which is transformed in vivo to the active form. Suitable prodrugs include esters, phosphonate esters etc, of the active form of the compound.

Additionally, compositions of the invention can be implanted into a patient or injected using a drug delivery system. Coated delivery devices can also be useful. See, for example, Urquhart, et al. (1984), *Ann. Rev. Pharmacol. Toxicol.* 24: 199-236; Lewis, ed. "Controlled Release of Pesticides and Pharmaceuticals" (Plenum Press, New York, 1981); U.S. Pat. Nos. 3,773,919; 6,747,014; and 35 3,270, 960.

In certain embodiments, the compositions are delivered using a device, or bandage, used for example in the process of treatment of a wound.

The therapeutically effective amount of a pharmaceutical compositions disclosed herein for any particular subject will depend upon a variety of factors including: the toxicity and therapeutic efficacy of the pharmaceutical composition; the severity of the ailment; the age, body weight, general health, sex and diet of the patient; the time of administration; the route of administration; the rate of sequestration of the compositions; the duration of the treatment; drugs used in combination or coincidental with the treatment, together with other related factors well known in medicine.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

Data obtained from the cell culture assays and animal models described herein can be used in formulating a range of therapeutically effective dosages for use in humans. The dosage of such compounds lies preferably within a range of circulating concentrations that include the $ED_{50}$ with little or no toxicity. The dosage can vary within this range depending upon the dosage form employed and the route of administration utilized.

The amount of compound of the invention described herein which can be combined with a carrier material to produce a dosage form will generally be that amount of the compound which produces a therapeutic effect. Generally, out of one hundred percent, this amount will range from about 0.1% to 99% of compound, preferably from about 5% to about 70%, most preferably from 10% to about 30%.

The dosage can be determined by a physician and adjusted, as necessary, to suit observed effects of the treatment. By way of illustration only the compositions may be administered so that the pharmaceutical acceptable compositions is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100

µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg etc. . . . . It is to be further understood that the ranges intermediate to the given above are also within the scope of the methods and compositions described herein, for example, in the range 1 mg/kg to 10 mg/kg, dose ranges such as 2 mg/kg to 8 mg/kg, 3 mg/kg to 7 mg/kg, 4 mg/kg to 6 mg/kg etc.

Where the compound of the invention is CBS, mCBS or mCBS.Na the dosage may be from 10 to 800 µg/ml. Preferably, it is in the range of 50 to 500 µg/ml. More preferably the dosage is 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790 or 800 µg/ml when administered to a human subject.

In certain examples of the invention an effective amount of the modified sulfated cellobioside compound is given as a single dose of administration. In certain examples, the dose is given repeatedly. That is treatment regimens will vary depending on the severity and type of disease, the overall health and age of the patient, and various other conditions to be considered by the treating physician. With respect to duration and frequency of treatment, it is typical for skilled clinicians to monitor subjects to determine when a treatment is providing therapeutic benefit, and to determine whether to increase or decrease dosage, increase or decrease administration frequency, discontinue treatment, resume treatment or make other alteration to treatment regimen.

Therapeutics or pharmaceutical acceptable compositions of the invention according to any aspect, embodiment or example described hereof, may be provided in a single bolus administration or in multiple doses or treatments and may also be applied by "continuous" therapy where a small amount of the therapeutic composition is provided continually over an extended time period.

Where multiple dosing is used in the treatment (including continuous therapy) the therapeutics or pharmaceutical composition will be administered by a dosing schedule that can vary from once a week to daily depending on several clinical factors, such as the subject's sensitivity to the modified sulfated cellobioside compound used in the therapeutic or pharmaceutical composition. The desired dose to be administered in such a regime can be delivered as a single dose at one time or divided into sub-doses, e.g., 2-4 sub-doses and administered over a time period, e.g., at appropriate intervals through the day or other appropriate schedule. Such sub-doses can be administered as unit dosage forms.

In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The desired dose can be administered using continuous infusion or delivery through a controlled release formulation. In that case, the pharmaceutical composition contained in each sub-dose must be correspondingly smaller to achieve the total daily dosage.

The dosage unit can also be compounded for delivery over several days, e.g., using a conventional sustained release formulation which provides sustained release of the pharmaceutical composition over a several day period. Sustained release formulations are well known in the art and are particularly useful for delivery of agents at a site, such as could be used with the agents described herein. In this embodiment, the dosage unit contains a corresponding multiple of the daily dose.

4. Combination Regimes

In certain exemplary embodiments, according to the fifth aspect of the invention, the identified composition may also comprise a second active agent, compound or composition selected from: one or more of anti-inflammatory agents, antibiotic agents, antiviral agents, antifungal agents and/or any other form of therapeutic or pharmaceutical compound that treats one or more conditions that the subject is afflicted with. According to this embodiment, the second active agent, compound or composition desirably provides an adjunct therapy for sepsis, SIRS and IRI or for a medical condition or disease associated with sepsis, SIRS and IRI. Preferably, the second active agent, compound or composition comprises one or more of anti-inflammatory agents.

Therapeutic advantages may be realised through combination regimens. In certain embodiments of the invention, the described methods may further comprise the step of: administering to a subject, at the same time or concomitantly with the inventive treatment, a second active agent that is an adjunct treatment for the sepsis, SIRS and IRI or the medical condition or disease associated with sepsis, SIRS and IRI that the patient is having or suffering from or is at risk of having or suffering from when delivered preventatively.

The second active agent may include, without limitation, anti-inflammatory agents, antibiotic agents, antiviral agents, antifungal agents or other forms of medical intervention that is distinct from the compound of the invention.

By way of illustration, when the method or treatment is directed to treating or ameliorating a septic or non-septic disease state involving NET mediated pathology in a subject the method may also comprise administering to a subject at the same time or concomitantly, a second anti-inflammatory agents, antibiotic agents, antiviral agents, antifungal agents or other forms of medical intervention that is distinct from the compound of the invention, which provides an adjunct treatment for a medical condition involving NET mediated pathology.

In one example, the second active agent provides an adjunct treatment or prevention for sepsis, SIRS or IRI or the medical condition or disease associated with the sepsis, SIRS or IRI such as a sepsis, SIRS or IRI or a medical condition or disease associated with the sepsis, SIRS or IRI involving NET mediated pathology in a subject.

In another example, the second active agent provides an adjunct treatment or prevention for a medical condition involving NET cytotoxicity.

By way of illustration, when the method of treatment is directed to treating or ameliorating a septic or non-septic disease state associated with sepsis, SIRS or IRI involving NET mediated pathology in a subject, the method may also comprise administering to a subject at the same time or concomitantly, a second anti-inflammatory agents, antibiotic agents, antiviral agents, antifungal agents or other forms of medical intervention that is distinct from the compound of the invention, which provides an adjunct treatment for a medical condition involving NET mediated pathology.

In some examples, the additional agent administered is an anti-inflammatory agent such as a steroid, corticosteroids, COX-2 inhibitor, non-steroidal anti-inflammatory agent (NSAIDs), aspirin or any combination thereof. More particularly, the additional agent administered may be an anti-inflammatory agent, selected from the group consisting of Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone, Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium, and combinations thereof.

In some examples, the additional agent administered is an antibiotic agent such as kanamycin, actinomycin D, doxorubicin, bleomycin, mithramycin, aminoglycosides, ansamycins, carbacephems, carbapenems, cephalosporins, glycopeptides, lincosamides, macrolides, monobactams, penicillins, polypeptides, quinolones sulfonamides and/or tetracyclines.

In some examples, the additional agent administered is an antiviral agent such as a non-nucleoside reverse transcriptase inhibitor, nucleoside reverse transcriptase inhibitor (e.g. nucleoside analogues), protease inhibitor and/or a nucleotide analogue reverse transcriptase inhibitor.

In some examples, the additional agent administered is an antifungal agent such as an imidazole, triazole, thiazole, allylamine, and/or echinocandin compound.

In some examples, the additional agent administered is an agent to treat diabetes. Such agents include those agents known in the art for treatment of diabetes and or for having anti-hyperglycemic activities, for example, inhibitors of dipeptidyl peptidase 4 (DPP-4) (e.g., Alogliptin, Linagliptin, Saxagliptin, Sitagliptin, Vildagliptin, and Berberine), biguanides (e.g., Metformin, Buformin and Phenformin), peroxisome proliferator-activated receptor (PPAR) modulators such as thiazolidinediones (TZDs) (e.g., Pioglitazone, Rivoglitazone, Rosiglitazone and Troglitazone), dual PPAR agonists (e.g., Aleglitazar, Muraglitazar and Tesaglitazar), sulfonylureas (e.g., Acetohexamide, Carbutamide, Chlorpropamide, Gliclazide, Tolbutamide, Tolazamide, Glibenclamide (Glyburide), Glipizide, Gliquidone, Glyclopyramide, and Glimepiride), meglitinides ("glinides") (e.g., Nateglinide, Repaglinide and Mitiglinide), glucagon-like peptide-1 (GLP-1) and analogs (e.g., Exendin-4, Exenatide, Liraglutide, Albiglutide), insulin and insulin analogs (e.g., Insulin lispro, Insulin aspart, Insulin glulisine, Insulin glargine, Insulin detemir, Exubera and NPH insulin), alpha-glucosidase inhibitors (e.g., Acarbose, Miglitol and Voglibose), amylin analogs (e.g. Pramlintide), Sodium-dependent glucose cotransporter T2 (SGLT T2) inhibitors (e.g., Dapgliflozin, Remogliflozin and Sergliflozin) and others (e.g. Benfluorex and Tolrestat).

Those skilled in the art will appreciate that the compositions according to any aspect, embodiment or example described hereof may be administered as part of a combination therapy approach to the treatment of sepsis, SIRS or IRI or a disease or condition associated with sepsis, SIRS or IRI. In combination therapy, the respective agents may be administered simultaneously, or sequentially in any order. When administered sequentially, it may be preferred that the components be administered by the same route.

In some examples where the two agents are applied separately, one would generally ensure that a significant time period did not expire between the time of each delivery, such that both agents would still be able to exert an advantageously combined effect. In such instances, it is contemplated that one would typically administer both modalities within about 12-24 hours of each other and, more preferably, within about 6-12 hours of each other, with a delay time of only about 12 hours being most preferred, in some situations, it may be desirable to extend the time for treatment significantly, however, where several days (2, 3, 4, 5, 6 or 7) to several weeks (1, 2, 3, 4, 5, 6, 7 or 8) lapse between the respective administrations. It also is conceivable that more than one administration of a drug will be desired.

When compositions of the invention, and a second active agent are administered in different compositions, routes of administration may be different. For example, the composition of the invention is administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration, and the second pharmaceutically active agent is administration by a different route, e.g. a route commonly used in the art for administration of said pharmaceutically active agent. In a non-limiting example, the compositions of the invention can be administered by injection, while the second active agent can be administrated orally.

5. Manufacture of a Medicament

In a sixth aspect of the invention, there is provided a use of a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof, in the manufacture of a medicament for treating a medical condition, ailment or disease involving NETs.

Preferably in this aspect of the invention the selected compound is a polyanionic sulfated cellobioside modified with a small uncharged glycosidically linked substituent at the reducing terminus. More preferably, the small uncharged glycosidically linked substituent improves the chemically stability of the polyanion, relative to the same polyanion that is sulfated at its reducing terminus. In particular, when the compound is mCBS it is a sulfated β-O-methyl cellobioside disaccharide or a sodium salt of β-O-Methyl Cellobioside Sulfate, viz mCBS.Na.

For example, in an embodiment of the sixth aspect of the invention, there is provided a use of a therapeutically or pharmaceutically effective amount of a polyanionic sulfated cellobioside or a polyanionic sulfated cellobioside modified with a small uncharged glycosidically linked substituent at its reducing terminus or a pharmaceutically acceptable salt thereof, in the manufacture of a medicament for the treatment or prevention of sepsis or an IRI or a medical condition or disease associated with sepsis, SIRS or IRI in a subject. Preferably, the modified sulfated cellobioside is mCBS or more particularly is a pharmaceutically acceptable salt thereof such as mCBS.Na.

In one embodiment of such use, the medicament is for the treatment of sepsis or SIRS or of a medical condition or disease associated with sepsis or SIRS in a subject, wherein said treatment ameliorates or inhibits said sepsis or SIRS or said condition or disease associated with said sepsis or SIRS.

In another embodiment of such use, the medicament is for the treatment of an IRI or of a medical condition or disease associated with an IRI in a subject, wherein said treatment ameliorates or inhibits said the IRI or said condition or disease associated with said injury.

In yet another embodiment of such use, the medicament is used to neutralise NETs that (i) are cytotoxic towards the endothelium in a subject, or (ii) contribute to endothelial dysfunction in a subject, or (iii) initiate coagulation by activating platelets in a subject, or (iv) induce red cell fragility and resultant anaemia in a subject.

In yet another embodiment, the manufactured medicament may also include a therapeutic or pharmaceutically effective amount of a second active agent, compound or composition. According to this embodiment, the second active agent, compound or composition provides an adjunct therapy for treating a medical condition, ailment or disease involving NETs. Desirably, the second active agent, compound or composition provides an adjunct therapy for the treatment of sepsis, SIRS or IRI or for a medical condition or disease associated with sepsis, SIRS or IRI. Preferably, the second active agent is selected from: one or more of anti-inflammatory agents, antibiotic agents, antiviral agents, antifungal agents and/or any other form of therapeutic or pharmaceutical compound that treats one or more conditions that the subject is afflicted with. More preferably, the second active agent, compound or composition comprises one or more of anti-inflammatory agents.

When the modified sulfated cellobioside compound is used in any of the methods of the invention the compound can be administered or formulated for administration to the subject in need thereof, in a single dose of formulation. In certain alternative embodiments, the modified sulfated cellobioside compound is administered, or formulated for administration to the subject in need thereof, as a multi-dose formulation.

Preferably, for administration to a subject, the therapeutic or pharmaceutical composition is provided as a pharmaceutically acceptable composition. When in this form, (1) the composition will be pharmaceutical formulated together with one or more pharmaceutically acceptable carriers (additives) and/or diluents and/or excipients and (2) the modified sulfated cellobioside compound in the composition may be formulated in a neutral or salt form.

EXAMPLES

The present invention is described further in the following non-limiting example which is provided by way of illustration only, and should not be construed as limiting the generality of the disclosure of the description throughout this specification.

Example 1: Method for the Preparation of mCBS.Na

β-O-methyl cellobioside is prepared as described by Jon K Fairweather et al., 2004, *Aust. J. Chem.*, 57: 197-205.

β-O-methyl cellobioside sulfate (mCBS) and sodium β-O-methyl cellobioside sulfate (mCBS.Na) compounds were prepared as described by Katrin C Probst and Hans Peter Wessel, 2001, *J. Carbohydrate Chemistry*, 20 (7 & 8): 549-560, the disclosure of which is hereby incorporated herein by reference in its entirety.

β-O-methyl cellobioside sulfate (mCBS) was prepared according to the following schematic:

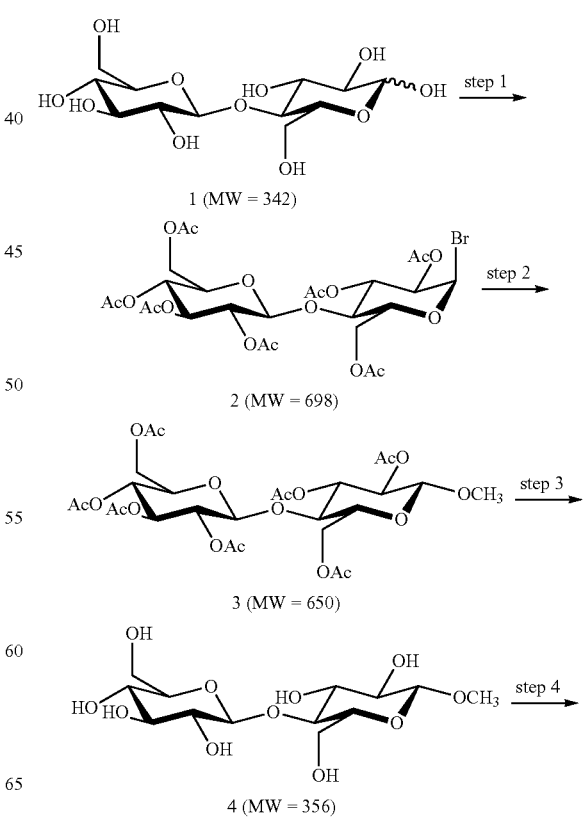

-continued

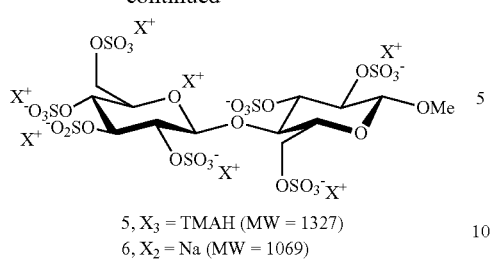

5, X₃ = TMAH (MW = 1327)
6, X₂ = Na (MW = 1069)

Step 1: To the mixture of α-D-cellobiose 1 (116 g, 338 mmol) and glacial acetic acid (1.6 L) was added acetyl bromide (300 mL, 500.0 g, 4065 mmol, 12.0 equiv) at room temperature. The resulting creamy mixture was heated at 60° C. for 45-55 mins until the reaction mixture turn to be a clear solution which indicate the completion of reaction.

Carefully pour the hot solution into the beaker (10 L) containing the cracked ice (4 kg). Stir the mixture until the white solid precipitated (~10 min). Add another portion of cold water (1 L) and keep on stirring for 10 min.

Filter with sinter funnel and washed the solid with cold water (700 mL×3). The resulting solid in the funnel was dissolved in DCM (1 L) and washed the funnel with DCM (300 mL×2). The combined DCM layer was washed with brine (1 0.5 L) and back extracted with DCM (0.5 L). The final DCM layer was dried over $Na_2SO_4$, filtered and concentrated under reduce pressure at <35° C. within 2 h to obtain the target bromide 2 (172.5 g, 74.3% yield) which was directly used for the following glycosylation.

Step 2: To the mixture of per-O-acetylated cellobiosyl bromide 2 (171 g, 250 mmol), anhydrous DCM (800 mL), anhydrous MeOH (800 mL), activated 3 A molecular sieves (70 g) was added silver carbonate ($Ag_2CO_3$, 75 g, 275 mmol, 1.1 equiv). The resulting mixture was stirred in the absence of light for 16 h. The mixture was purified through a plug of silica and eluted with EtOAc. The collected fractions were concentrated to give the crude product as the brown solid which was directly used for the next step. The $R_f$ of compound 3=0.28 (EtOAc-Hexane, 1:1).

Step 3: To the mixture of the crude product obtained from step 2 and anhydrous MeOH (1 L) was added a small piece of Na (1.72 g, 0.3 equiv, 75 mmol) at room temperature. Shortly afterwards, a white solid began to precipitate from solution. The resulting mixture was stirred overnight in order to ensure the completion of de-acetylation. The final suspension was filtered and washed with MeOH (300 mL×2). The white solid was collected and dried under vacuum for overnight to obtain the final cellobioside 4 (72.5 g, 81.4% over 2 steps).

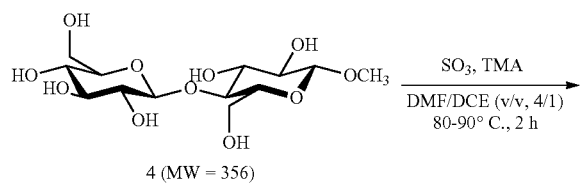

4 (MW = 356)

-continued

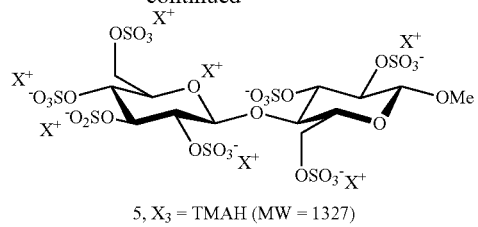

5, X₃ = TMAH (MW = 1327)
6, X₂ = Na (MW = 1069)

Synthetic and Purification Procedure for Step 4:
Step 4 The mixture of compound 4 (84.0 g, 236 mmol), $SO_3$.TMA (367.4 g, 2.64 mol, 11.2 equiv), anhydrous DMF (3140 mL) and anhydrous DCE (767 mL) was degassed under Ar for three times and heated at 80-90° C. for 2 h. (Reaction monitoring: After heating for 10 min, the creamy mixture turned to be a clear solution. After 30 min, the solution became cloudy again. After 50 min, the aggregated solid was observed on the surface of flask.) Upon cooling, the resulting mixture was moved to the cold room (−5° C.) and settled overnight which allows the solid to completely aggregate from the solvent. The complete conversion from compound 4 into 5 was confirmed with 1H-NMR. Decant the solution into the drain. The crude solid was filtered and washed with DCM for a couple of times. The resulting solid was dissolved in de-ionized water and directly subjected to ion-exchange column [Na form of DOWEX 50 W×8: 3 kg of resin ($H^+$ form) was pre-packed in glass gravity column, regenerated by elution of 1M NaOH (~6 L) and neutralized with de-ionized water (~12 L)]. The collected fractions were concentrated to yield the final sulfated cellobioside 6 (232.1 g, 92.0%) as the glassy solid.

Examples 2 to 6: Comparison of CBS, mCBS and MTS

In the following studies, the inventors examined 3 SPAs, namely cellobiose per-O-sulfate (CBS), methyl β-cellobioside per-O-sulfate (mCBS) and maltotriose per-O-sulfate (MTS) (structures in FIG. 1). The methodologies used in Examples 2 to 6 are set out below.

Method and Materials for the Following Examples (2-6)

Heparin (porcine mucosa—PM) was purchased from Sigma-Aldrich.

Human subjects. All human-related research was approved by the ACT Health Human Research Ethics Committee. Healthy adult donors were used as a source of erythrocytes and platelets for in vitro studies. Consenting patients admitted to The Canberra Hospital Intensive Care Unit with an APACHE II mortality score ≥12 (Knaus, W. A., Draper, E. A., Wagner, D. P. & Zimmerman, J. E. APACHE II: a severity of disease classification system. *Crit care med* 13, 818-829 (1985)) on arrival in the ICU and a diagnosis of sepsis were included in our study.

Sepsis was diagnosed based upon the following criteria (Mayr, F. B., Yende, S. & Angus, D. C. Epidemiology of severe sepsis. *Virulence* 5, 4-11 (2014); and Bone, R. C. et al. Definitions for sepsis and organ failure and guidelines for the use of innovative therapies in sepsis. The ACCP/SCCM Consensus Conference Committee. American College of Chest Physicians/Society of Critical Care Medicine. *Chest* 101, 1644-1655 (1992)):

a. At least two of the following:
   i. Tachypnea >24 bpm, or blood gas PCO2<32 mm Hg
   ii. White blood cells count (WCC) either <4,000 cell/mm3 or >12,000 cells/mm3
   iii. Heart rate (HR) >100 bpm
   iv. Temperature (fever) >38.0° C. or (hypothermia) <36.0° C.
b. No alternative cause for Systemic Inflammatory Response Syndrome (SIRS) identified
c. Evidence of sepsis including positive blood culture, signs of pneumonia on chest x-ray or other imaging
d. Evidence of end-organ dysfunction: renal failure, liver dysfunction, changes in Glasgow Coma Score (not attributable to other causes) or raised serum lactate.
e. Refractory hypotension requiring inotropic support.

Animals. All animal experiments were approved by the Australian National University Animal Experimentation Ethics Committee. Pathogen free male and female C57BL/6 mice (6-8 weeks of age), female BALB/c mice (5-6 weeks of age) and male Wistar rats (weighing between 250-350 g) were obtained from the Australian Phenomics Facility at the Australian National University.

Cell line and cell culture conditions. Human microvascular endothelial cells-1 (HMEC-1), carrying the type O blood group and thus not reactive with anti-blood group antibodies in human sera, were supplied by ATCC and were cultured in MCDB 131 medium supplemented with 10% heat-inactivated fetal calf serum (FCS), 2 mM L-glutamine, 100 IU ml$^{-1}$ penicillin, 100 μg ml$^{-1}$ streptomycin, 10 ng ml$^{-1}$ EGF and 1 μg ml$^{-1}$ hydrocortisone. The cells were incubated in 5% $CO_2$ and ambient $O_2$ at 37° C. and were repeatedly tested for *mycoplasma* using a MycoAlert Assay kit (Lonza).

Histone-mediated cytotoxicity assays. To determine the cytotoxicity of calf thymus histones (Sigma-Aldrich), various concentrations of histones (100-800 μg ml$^{-1}$) were added to suspensions of HMEC-1 or HUVEC ($1\times10^6$ ml$^{-1}$) in 96 well plates and incubated for 1 h at 37° C. Cells were then incubated for 5 min at 37° C. with propidium iodide (PI; 2.5 μg ml$^{-1}$) (ThermoFisher Scientific), to detect dead cells, and Calcein-AM (0.04 μM) (ThermoFisher Scientific), to detect viable cells, placed on ice and the percentage of dead and viable cells determined by flow cytometry using gating strategies. In inhibition assays, HMEC-1 were incubated with histones (400 μg ml$^{-1}$) for 1 h at 37° C. in the presence of different concentrations of compounds (12.5-400 μg ml$^{-1}$) prior to the addition of PI and Calcein-AM. HMEC-1 cytotoxicity at each compound concentration was then determined based on the formula:

$$\text{Cytotoxicity (\%)} = \frac{\text{Dead (compound \& histones)} - \text{Dead (cells alone)} \times 100}{\text{Dead (histones alone)} - \text{Dead (cells alone)}}$$

and the IC50 value for each polyanion then determined based on the line of best fit (nonlinear regression analysis) using Prism Software (Graphpad Software). In all assays MTS (IC50 30 μg ml$^{-1}$) was included as a standard to compensate for experimental variation, with data being adjusted in each assay to MTS having an IC50 of 30 μg ml$^{-1}$.

Lipid bilayer assays. Artificial lipid bilayers, prepared as previously described (Rebbeck, R. T. et al. The beta(1a) subunit of the skeletal DHPR binds to skeletal RyR1 and activates the channel via its 35-residue C-terminal tail. *Biophys J* 100, 922-930 (2011).), separated symmetrical 150 mM or 250 mM KCl (pH ~5.5) solutions. Histones (1 μM, 15.2 μg ml$^{-1}$) were added to bilayers alone or after 0.5-3 h incubation with 10 μM CBS (3.5 μg ml$^{-1}$) or 10 μM MTS (5.1 μg ml$^{-1}$) at ~20° C. Current was recorded continuously after histone addition until the bilayers broke or the experiment was terminated.

Calcium flux studies in endothelial cells. HMEC-1 ($2\times10^7$ ml$^{-1}$) in RPMI-1640 medium were incubated with Indo-1 AM (5 μM) (ThermoFisher) (Tellam, R. L. & Parish, C. R. The effect of sulfated polysaccharides on the free intracellular calcium ion concentration of lymphocytes. *Biochim Biophys Acta* 930, 55-64 (1987); and Weston, S. A., Tellam, R. L. & Parish, C. R. Dextran sulfate induces changes in the free intracellular calcium ion concentration of a subpopulation of immature thymocytes. *Immunol Cell Biol* 69, 369-376 (1991)) at 37° C. for 60 min. After 3 washes with RPMI-1640 medium supplemented with 5% FCS the cells were resuspended at $4\times10^6$ ml$^{-1}$ in ice-chilled HEPES-buffered saline (NaCl 8 g l$^{-1}$, KCl 0.4 g l$^{-1}$, $CaCl_2$ 0.2 g l$^{-1}$, $MgCl_2 \cdot 6H_2O$ 0.2 g l$^{-1}$, D-glucose 1.8 g l$^{-1}$, pH 7.4) supplemented with 10 mM HEPES. The cell suspension was kept on ice and used within 3 h. Intracellular $Ca^{2+}$ flux was monitored using flow cytometry. The cells were pre-equilibrated and maintained at 37° C. during analysis using an external sheath connected to a heated water bath. After the exclusion of cellular debris and clumped cells (on the basis of FSC/SSC light scattering) the basal $Ca^{2+}$ level was monitored for 2 min before histone addition in the presence/absence of novel compounds. $Ca^{2+}$ levels were measured at 1, 3 and 9 min post-histone addition with a constant flow rate (~300 events/sec). $Ca^{2+}$ flux was determined as an increase in the ratio of geometric mean fluorescence intensity (GMFI) of $Ca^{2+}$-bound over $Ca^{2+}$-unbound Indo-1.

In vitro erythrocyte microscopy, aggregation, fragility and deformability assays. Histone-mediated aggregation of human erythrocytes and its inhibition by various compounds was detected by flow cytometry, based on either forward and side scatter parameters or erythrocyte auto-fluorescence, as reported by the inventors previously (Kordbacheh, F., O'Meara, C. H., Coupland, L. A., Lelliott, P. M. & Parish, C. R. Extracellular histones induce erythrocyte fragility and anemia. *Blood* 130, 2884-2888 (2017).) and scanning electron microscopy as described earlier (Yabas, M. et al. Mice deficient in the putative phospholipid flippase ATP11C exhibit altered erythrocyte shape, anemia, and reduced erythrocyte life span. *J Biol Chem* 289, 19531-19537 (2014)). Similarly, erythrocyte fragility induced by histones, in the presence or absence of inhibitors, was quantified using a sheer stress assay that we developed recently (Kordbacheh, F., O'Meara, C. H., Coupland, L. A., Lelliott, P. M. & Parish, C. R. Extracellular histones induce erythrocyte fragility and anemia. *Blood* 130, 2884-2888 (2017)). Finally, the reduced deformability of erythrocytes in the presence of histones and the effect of inhibitors on this process was assessed by measuring the passage of erythrocytes through an artificial human spleen (Kordbacheh, F., O'Meara, C. H., Coupland, L. A., Lelliott, P. M. & Parish, C. R. Extracellular histones induce erythrocyte fragility and anemia. *Blood* 130, 2884-2888 (2017); and Deplaine, G. et al. The sensing of poorly deformable red blood cells by the human spleen can be mimicked in vitro. *Blood* 117, e88-95 (2011)).

In vitro platelet aggregation and degranulation assays. For aggregation studies platelets were isolated from human whole blood collected into Na-citrate vacutainers through 2-step centrifugation at room temperature (200×g for 20 min then the platelet-rich plasma 800×g for 15 min), the platelet pellet resuspended in Hank's balanced salt solution containing calcium and magnesium and histones added and incubated in the presence/absence of compounds at the concentrations of each as indicated. Samples were assessed for degree of platelet aggregation after 15 min exposure to histones by flow cytometry using the characteristic log FSC versus log SSC identification of platelets, with increases in the geometric mean of log FSC indicative of platelet aggregation.

For the platelet activation assay, whole blood collected in Na-citrate vacutainers was monitored for platelet degranulation using the luminescence mode on the Chrono-Log Model 700 with Chrono-Lume reagent (Chrono-Log Corp). Saline (300 µl) was added to pre-warmed blood (420 µl) with a stirrer bar in-situ. Chromo-Lume reagent (100 µl) was then added and incubated for 2 min before histones±compounds diluted in water were added in a total volume of 180 µl at the concentrations indicated. Results expressed as ATP release calculated as a percentage of the histone+saline control.

In-vivo histone toxicity assays. BALB/c female mice (5-6 weeks of age), that are more prone to histone-induced anemia and easier to inject i.v. at this young age than C57BL/6 mice, were injected i.p. with test compounds at concentrations indicated 10 min prior to i.v. injection of histones (50 mg kg$^{-1}$) in phosphate buffered saline. Retroorbital bleeds were performed with glass Pasteur pipettes 10 min after histone injection and collected blood added to acid citrate dextrose (ACD), the 10 min blood sample being subjected to hematologic analyses for platelet and erythrocyte content using an ADVIA 2120i Hematology Analyzer. Spleens were also harvested at 10 min post-histone injection and splenic hemoglobin content quantified using a hemoglobin assay kit (Sigma-Aldrich). In the case of 4 h blood samples, male C57/BL/6 mice (6-8 weeks of age) were injected with test compounds and histones as above and plasma isolated and stored frozen for subsequent biochemical testing, with markers for liver (alanine aminotransferase, ALT), kidney (creatinine, Crea) and general tissue (lactate dehydrogenase, LDH) damage being determined by the Department of Pathology, The Canberra Hospital.

Murine deep vein thrombosis (DVT) model. The procedure used is largely as previously described (Brill, A. et al. Neutrophil extracellular traps promote deep vein thrombosis in mice. *J Thromb Haemost* 10, 136-144 (2012)). Briefly, 8 week old male C57BL/6 mice were anaesthetized, a laparotomy incision made, the intestines exteriorized and then, after gentle separation from the abdominal aorta, the inferior vena cava (IVC) immediately below the renal veins was ligated to ~10% patency and all associated IVC tributaries were ligated. The peritoneum and skin were closed following which all mice received an i.v. injection of histones via the tail vein (10 mg kg$^{-1}$) or an equivalent volume of saline followed 5 min later by an i.v. injection of test compounds (50 mg kg$^{-1}$) or saline. Mice were monitored for 48 h after which they were re-anesthetized, re-opened and any thrombi that had developed distal to the IVC stenosis were removed for analysis. Sham operated control animals received laparotomy and 90% ligation of the IVC, however the ligation was removed immediately after occlusion of the IVC.

Rat caecal ligation and puncture (CLP) assay for sepsis. The CLP assay was performed in male Wistar rats as previously described (Hubbard, W. J. et al. Cecal ligation and puncture. *Shock* 24 Suppl 1, 52-57 (2005)). Test compounds (50 mg kg$^{-1}$) dissolved in saline or an equivalent volume of saline only (Control cohort) were administered i.p. 5 min pre-CLP and 5, 10 and 15 h post-op until cessation of the experiment at 20 h. Sham-CLP rats underwent the same procedure, however, the caecum was not ligated or punctured and these rats received saline at the same times as above. At the conclusion of the experimental time period (20 h) or when morbidity required ethical euthanasia, the rats were anaesthetized and blood was collected via cardiac puncture into EDTA for subsequent analysis of liver (ALT) and kidney (creatinine) function by the Department of Pathology, The Canberra Hospital. The propensity for clots to form within the blood samples of the saline treated control CLP animals (despite the presence of EDTA) prevented successful analysis of plasma samples from all animals.

Rat cardiac ischemia reperfusion injury model. The method used is based on a combination of previously published procedures (Takada, Y., Hashimoto, M., Kasahara, J., Aihara, K. & Fukunaga, K. Cytoprotective effect of sodium orthovanadate on ischemia/reperfusion-induced injury in the rat heart involves Akt activation and inhibition of fodrin breakdown and apoptosis. *J Pharmacol Exp Ther* 311, 1249-1255 (2004); and Hale, S. L., Dae, M. W. & Kloner, R. A. Hypothermia during reperfusion limits 'no-reflow' injury in a rabbit model of acute myocardial infarction. *Cardiovasc Res* 59, 715-722 (2003)). Male Wistar rats were anaesthetized with isofluorane, intubated via tracheostomy and ventilated with a tidal volume of 1 ml 150 g$^{-1}$ and a respiratory rate of 65 breaths min$^{-1}$. Supplemental oxygen was delivered at a FiO$_2$ of ~30%. A left hemi-thoracotomy was performed to enable visualization of the left ventricle. The left coronary arterial plexus (LCA) was occluded using an atraumatic snare for 30 min prior to reperfusion for 30 min. Ischemia was confirmed by myocardial hyperemia. The test compounds (30 mg kg$^{-1}$) or an equivalent volume (200 µl) of saline were injected into the lumen of the left ventricle (confirmed with aspiration) 5 min prior to the release of the snare for the reperfusion phase.

At the conclusion of reperfusion (30 min), Thioflavin S (1 ml 200 g$^{-1}$ of body weight) was slowly injected into the lumen of the left ventricle, to define the territory of microvascular obstruction (MVO) within the ischemic zone (IZ). The IZ territory was determined by the re-occlusion of the atraumatic snare and infusion of blue microspheres into the left ventricle (Unisperse Blue, BASF), distributed within solutions via ultrasonication using a CD-6800 (Unisonics) sonicator. The heart was then excised from the thorax, rinsed in isotonic saline and 2 mm sections were cut distal to the atraumatic snare at right angles to the interventricular line. This method produced 4 myocardial sections which were weighed and photographed (Sony Handycam, Zeiss 60× optical zoom) under ultraviolet light (territory of MVO) and bright light (IZ territory), before being incubated in tetrazolium chloride (TTC) to determine the region of necrotic myocardium. Planimetry (Image J, Freeware) was used to quantify the areas of the IZ, MVO and necrosis.

Rat ischemia reperfusion tissue flap model. The procedure employed is largely based on a previously described method (Bone, R. C. et al. Definitions for sepsis and organ failure and guidelines for the use of innovative therapies in sepsis. The ACCP/SCCM Consensus Conference Committee. American College of Chest Physicians/Society of Critical Care Medicine. *Chest* 101, 1644-1655 (1992)). Briefly, male Wistar rats were anaesthetized, locally depilated and a 3 cm by 6 cm fasciocutaneous flap was excised leaving the vascular pedicle intact. The inferior epigastric artery was clamped, a fine rubber sheet was placed under the flap preventing oxygen diffusion from the tissues below and the flap was re-sutured back into place. The clamp was removed 10 h post-application permitting returned blood flow to the flap. Test compounds (50 mg kg$^{-1}$) or saline were administered i.p. 5 min prior to clamp application and 5 min following its removal. The rats were monitored for a total experimental period of 72 h during which rats received additional compound or saline i.p. at 24 and 48 h post-op. The 'Control No Clamp' rats had the tissue flap excised and rubber placed underneath prior to re-suturing, however, the vessel was not clamped and they received saline at the same time points as the other rats. At the end of the experimental period the viability of the flaps was determined by the percentage of black necrotic or reddened areas versus pink viable areas. Despite the application of Elizabethan collars and the use of analgesia as a settling agent, a small number of rats had to be prematurely euthanized when they repeatedly auto-cannibalized their flaps.

Quantification of DNA in patient sera. Blood from consenting patients with an APACHE II score >12 upon arrival at ICU was collected from venous access lines into a serum-separator tube, the tubes centrifuged at 2300×g for 10 min and the serum harvested and stored at −80° C. To quantify DNA content serum from septic patients (5 µl) was incubated with 95 µl of 5 µM Sytox Green at 37° C. for 10 min in a 96-well flat bottom culture plate. Fluorescence intensity was then measured in a fluorescence plate reader (Tecan Infinite M200 Pro) with excitation set at 504 nm and emission at 523 nm.

Detection and analysis of cytotoxicity of septic patient sera for endothelial cells. To measure the cytotoxic activity of septic patients sera for endothelial cells in-vitro, HMEC-1 were seeded into 96-well plates at $2.5 \times 10^4$ well$^{-1}$ in medium and grown at 37° C. in 5% $CO_2$ for 48 h prior to the addition of 50 µl of patient serum in the presence/absence of DNase I (10 µg ml$^{-1}$), anti-human histone 3 and histone 4 rabbit pAbs (200 µg ml$^{-1}$) (BioVision), or test compounds (200 µg ml$^{-1}$) and incubated for 3 h. $^3$H-thymidine (0.5 µCi, MP Biomedical) was then added to each culture well in 20 µl of HMEC-1 medium and incubated for a further 24 h. At the conclusion of the incubation period plates were subjected to 3 freeze/thaw cycles (−70° C. for 30 min, then 37±0.5° C. for 30 min) prior to harvesting and measurement of $^3$H-thymidine incorporation. Using a Filtermate 196 harvester (Packard Bioscience), cell cultures were harvested onto glass fiber filters (EasyTab™-C Self Aligning Filters; Packard Bioscience). Filters were dried at 80° C. and placed in Omnifilter plates (Perkin Elmer) then 20 µl of Microscint-O scintillation fluid (Perkin Elmer) was added to each well and the plate sealed with TopSeal-A adhesive film (Perkin Elmer). $^3$H-thymidine incorporation was measured using a TopCount NXT™ Microplate Scintillation and Luminescence Counter (Packard Bioscience). Results expressed as a percentage of the proliferation of HMEC-1 not exposed to patient sera.

Statistical analysis. Prism software (Graphpad Software) was used to perform statistical tests and to generate graphs, with details of the test used included in Figure legends.

In-Vitro Evidence of the Biological Effects of mCBS

The following Examples 2 to 6 provide in vitro evidence of the biological effect of mCBS in neutralising free histones and NETs.

Figure 2:
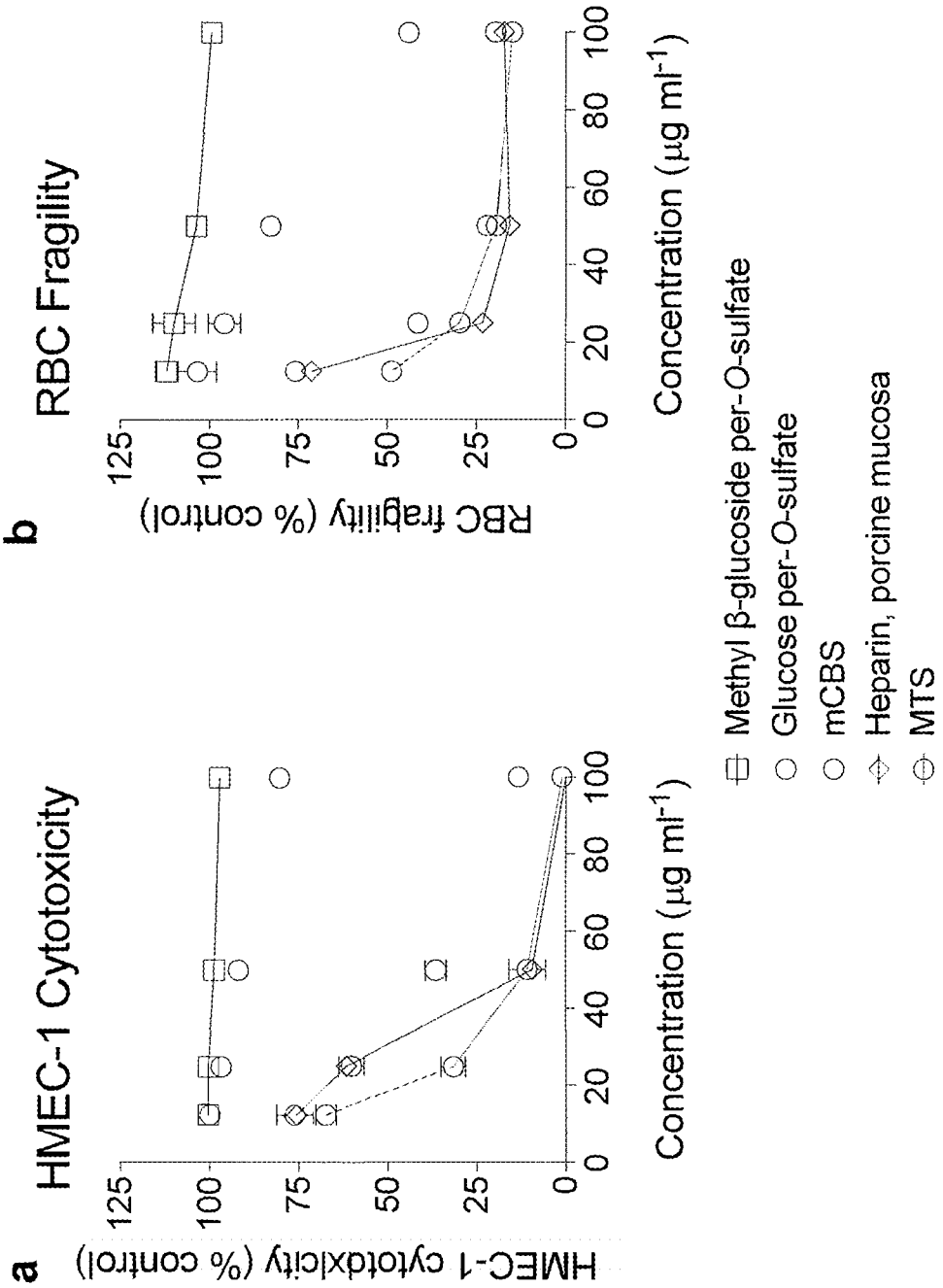
FIG. 2 Minimal structural requirements for polyanions to be as potent as heparin at inhibiting histone-mediated pathologies. a, Inhibition curves showing that the sulfated disaccharide, mCBS, and the sulfated trisaccharide, MTS, are as effective as heparin at inhibiting histone-mediated cytotoxicity for HMEC-1, whereas the sulfated monosaccharides, glucose per-O-sulfate and methyl β-glucoside per-O-sulfate, exhibit little or no inhibitory activity. b, Similar results obtained when examining inhibition of histone-induced erythrocyte fragility. Data are mean±s.e.m. (n=3 biological replicates).

Example 2: mCBS Protects Endothelial Cells from Histone Toxicity and Erythrocytes from Histone-Induced Fragility and Aggregation Each of CBS, mCBS and MTS (collectively called Small Polyanions or SPAs) have histone-inhibitory activity similar to heparin, unlike sulfated monosaccharides that are much less active, when histone cytotoxicity for endothelial cells (FIG. 2a) or induction of erythrocyte (RBC) fragility (FIG. 2b) was measured.

Figure 3:
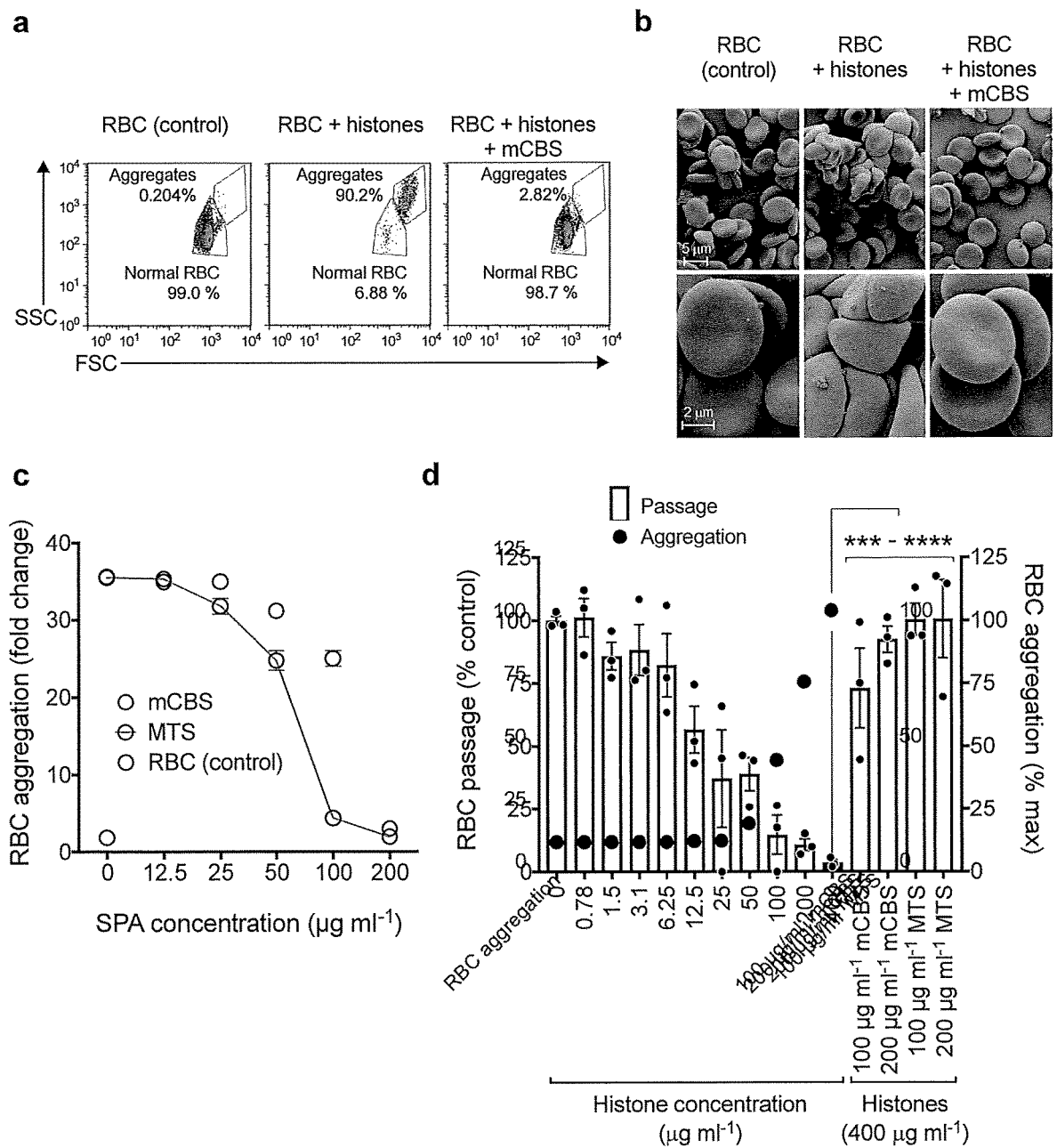
FIG. 3 Histones promote erythrocyte aggregation and reduce erythrocyte deformability, processes that are completely inhibited by SPAs. Human erythrocytes (RBC) were incubated for 1 h at 37° C. alone ('Saline' control) or in the presence of histones (400 μg ml$^{-1}$) with or without mCBS (200 μg ml$^{-1}$). a, Percentage of RBC aggregation measured by flow cytometry based on forward (FSC) and side (SSC) scatter parameters and an appropriate gating strategy to discriminate aggregated from normal (non-aggregated) RBC. b, Scanning electron micrographs depicting level of RBC aggregation at low and high magnification following the three treatments depicted in (a). c, Concentration dependent inhibition of histone-mediated RBC aggregation by mCBS and MTS, in this case RBC aggregation being calculated by flow cytometry as fold increase in RBC auto-fluorescence relative to RBC in the absence of histones. The fold increase values also provide an estimate of the number of RBC in each aggregate. d, Retention of RBC in an artificial spleen that measures RBC deformability. RBC were incubated with increasing concentrations of histones for 1 h and, at the highest concentration used (400 μg ml$^{-1}$), also incubated with either mCBS or MTS (100 and 200 μg ml$^{-1}$), prior to passage through the artificial spleen. Data are mean±s.e.m. (n=3 biological replicates). *P<0.001, **P<0.0001 (one way ANOVA with Dunnett's multiple comparisons test).

This Example investigates whether mCBS and MTS promote erythrocyte aggregation and reduce erythrocyte deformability. Based on flow cytometry FSC and SSC, histones very efficiently aggregate erythrocytes, this effect being completely inhibited by mCBS (FIG. 3a), a result confirmed by scanning EM (FIG. 3b). The inventors also used erythrocyte auto-fluorescence to quantify the number of erythrocytes present in histone-induced aggregates. At high histone concentrations (400 µg ml$^{-1}$) there were ~35 erythrocytes/aggregate, but mCBS and MTS prevented aggregation in a concentration dependent manner, with MTS being ~2-fold more effective than mCBS (FIG. 3c). Finally, erythrocytes exposed to histone concentrations that do not induce erythrocyte aggregation (<50 µg ml$^{-1}$) (FIG. 3d) showed significantly reduced passage through an artificial spleen, this assay measuring erythrocyte deformability/rigidity (Deplaine, G. et al. The sensing of poorly deformable red blood cells by the human spleen can be mimicked in vitro. *Blood* 117, e88-95 (2011)). The addition of mCBS and MTS, however, totally restored the ability of erythrocytes to passage through an artificial spleen (FIG. 3d), indicating that SPAs, as well as protecting erythrocytes from histone-mediated aggregation and fragility, prevent histone-induced rigidity.

Example 3: SPAs Inhibit Platelet Activation by Histones

Figure 4:
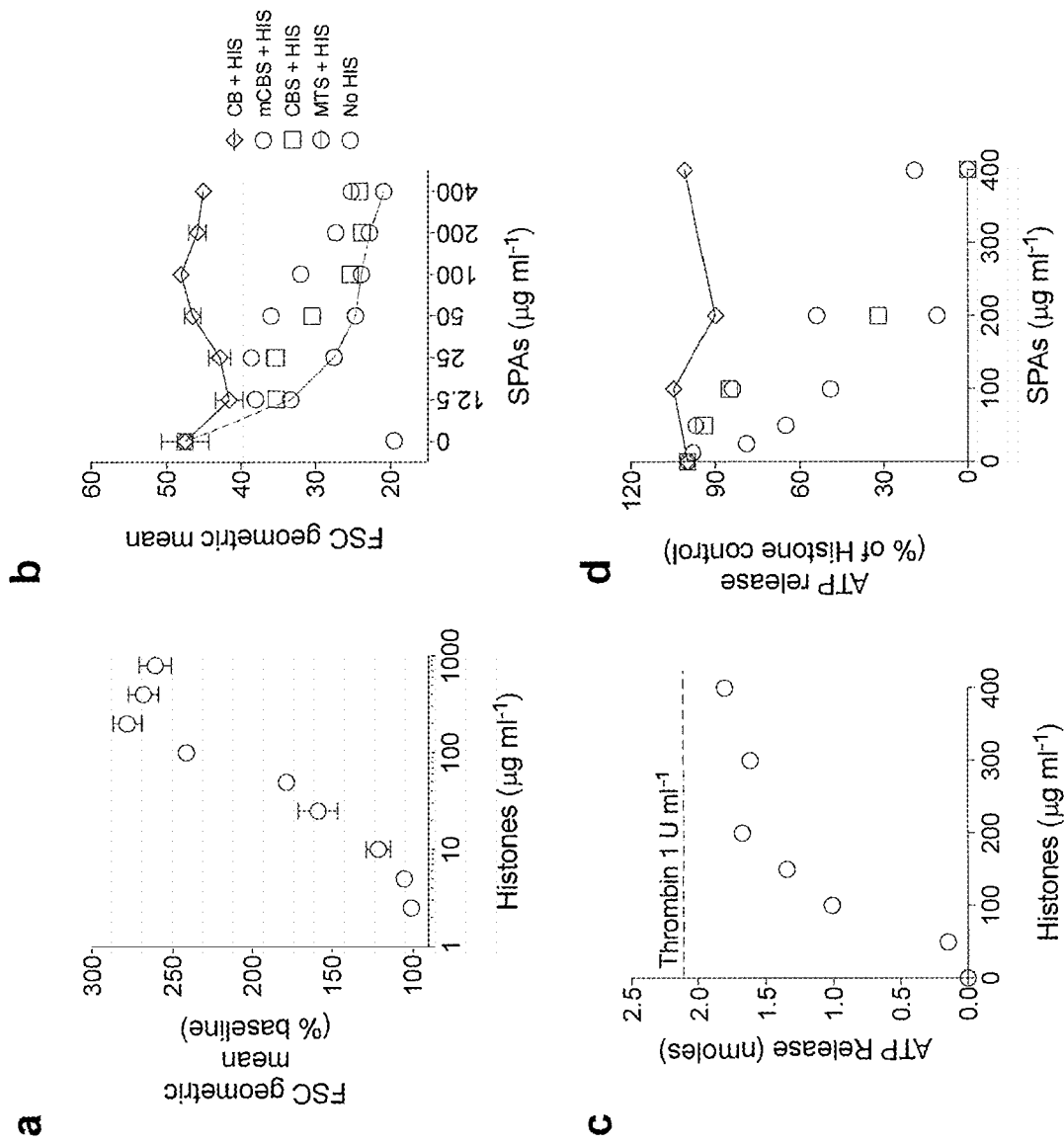
FIG. 4 SPAs inhibit histone-induced platelet aggregation and degranulation. a, Histone-induced aggregation of isolated platelets. b, SPA inhibition of histone (HIS)(150 μg/mL) induced platelet aggregation. c, Histone-induced degranulation of platelets in whole blood, as measured by ATP release. Dotted line ATP release from thrombin-activated platelets. d, SPA inhibition of histone-induced platelet degranulation. Data in (a,b) are mean±s.e.m (n=3 biological replicates). Data in (c,d) representative of one of three experiments.

Histones are known to induce platelet activation thus, to investigate the capacity of SPAs to inhibit this process, isolated, washed human platelets were incubated with histones and platelet aggregation measured by flow cytometry. Additionally, ATP release, due to platelet degranulation, was measured following exposure of whole blood to histones. Both platelet aggregation and degranulation were histone-concentration dependent (FIG. 4a, c), the difference in histone sensitivity of platelets between the two assays being attributed to the presence of plasma proteins and erythrocytes in the ATP release assay that also bind histones. Histone-induced platelet aggregation was completely inhibited by CBS, mCBS and MTS, with MTS being the most active (FIG. 4b). Unsulfated CB, included as a negative control, was non-inhibitory (FIG. 4b). Similar results were obtained with histone-induced ATP release (FIG. 4d). Thus, CBS, mCBS and MTS are effective in inhibiting the platelet-activating properties of histones.

Example 4: SPAs Prevent Lipid Bilayer Disruption

Figure 5:
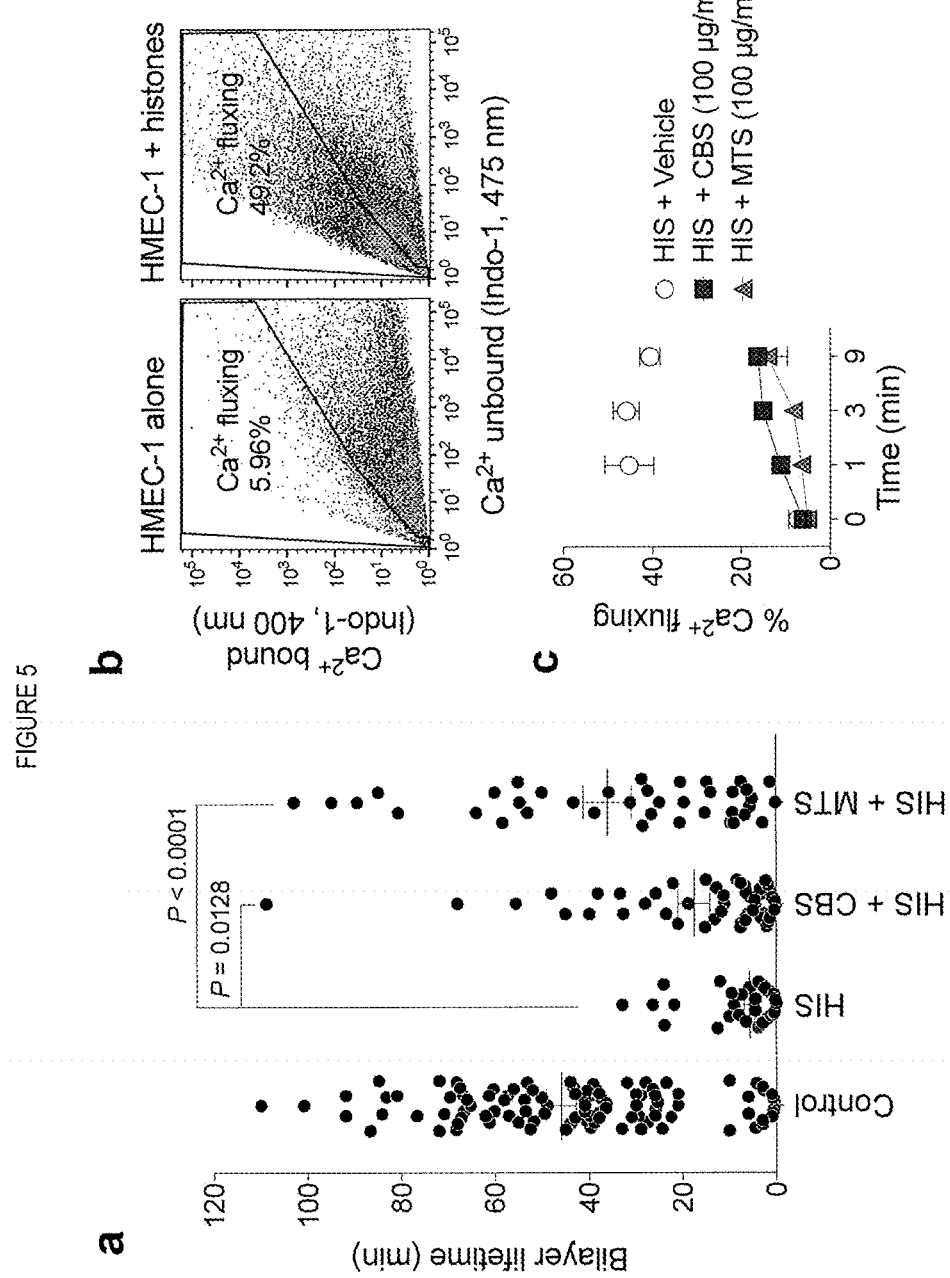
FIG. 5 Histones disrupt lipid bilayers and induce a cellular Ca$^{2+}$ flux, processes blocked by SPAs. a, Lifetime of artificial lipid bilayers exposed to histones (HIS)(1 μm) alone (n=47) or in the presence of the SPAs CBS (n=52) or MTS (n=40)(10 μM). Control bilayers (n=125) contained the RyR1 ion channel protein (n=biological replicates). Data are mean±s.e.m. P values calculated using non-parametric Kruskal-Wallis test. b, Representative flow cytometry plots, using Ca$^{2+}$ sensitive dye Indo-1, showing Ca$^{2+}$ fluxing HMEC-1 1 min following histone addition (100 μg ml$^{-1}$). c, Time course of effect of CBS and MTS (100 μg ml$^{-1}$) on histone-induced Ca$^{2+}$ flux by HMEC-1. Data in (c) from one of two separate experiments and mean of two biological replicates.

We next investigated how histones mediate their cytotoxicity and, consequently, how SPAs protect cells from histone-mediated damage. Histones are known to interact with and damage lipid bilayers (Kleine, T. J., Lewis, P. N. & Lewis, S. A. Histone-induced damage of a mammalian epithelium: the role of protein and membrane structure. *Am J Physiol* 273, C1925-1936 (1997)) and act as cell penetrating proteins (Rosenbluh, J. et al. Translocation of histone proteins across lipid bilayers and *Mycoplasma* membranes. *J Mol Biol* 345, 387-400 (2005)). Thus, we investigated whether histones mediate their cytotoxicity by directly disrupting lipid bilayers. To examine this possibility artificial lipid bilayers were prepared and their susceptibility to histone rupture detected by changes in current across the bilayers. Lipid bilayers have a finite lifetime, normally ~30 to 120 min (Rebbeck, R. T. et al. The beta(1a) subunit of the skeletal DHPR binds to skeletal RyR1 and activates the channel via its 35-residue C-terminal tail. *Biophys J* 100, 922-930 (2011)). In inventors experiments, control lipid bilayers containing ryanodine receptor 1 (RyR1) ion channel protein had an average lifetime of 46±4 min, addition of histones (1 µM) markedly reducing the lifetime to 5.7±1.2 min (FIG. 3a). In fact, 13/47 bilayers (28%) broke within 0.3-0.5 min of histone addition whereas only 2/125 control bilayers (1.6%) ruptured in the same time period, with higher histone concentrations (≥50 µM) resulting in rapid rupture of most bilayers (not shown). Bilayers were less prone to rupture by histones when CBS or MTS was present, the average bilayer lifetime increasing significantly to 18±4 min and 36±5 min for CBS and MTS, respectively (FIG. 5a). Furthermore, bilayer lifetimes with MTS were not significantly different from the control lifetimes. Similarly, compared with histones alone (28%), the incidence of rapid bilayer rupture decreased to 3/52 bilayers (5.8%) for CBS and 1/40 bilayers (2.5%) for MTS.

Earlier studies demonstrated that histones can induce non-selective $Ca^{2+}$ channels in cells and plasma membrane depolarisation. These findings further support the concept that histones directly interact with cell surface phospholipids and disrupt membrane integrity. To investigate whether CBS, mCBS and MTS protect cells against histone-induced $Ca^{2+}$ flux, HMEC-1 were loaded with the $Ca^{2+}$ sensitive dye, Indo-1, challenged with histones in the presence or absence of CBS or MTS, and $Ca^{2+}$ uptake measured by flow cytometry (FIG. 5b). Histones induced an over 8-fold increase in the population of cells exhibiting high intracellular $Ca^{2+}$ levels, this response plateauing 1 to 3 min after histone addition. The presence of MTS totally ablated the $Ca^{2+}$ response and CBS substantially inhibited the response (FIG. 5c). Collectively inventors findings indicate that histones damage cell membranes by directly disrupting the lipid bilayer of cells, with CBS, mCBS and MTS SPAs neutralising this undesirable property of histones.

Figure 6:
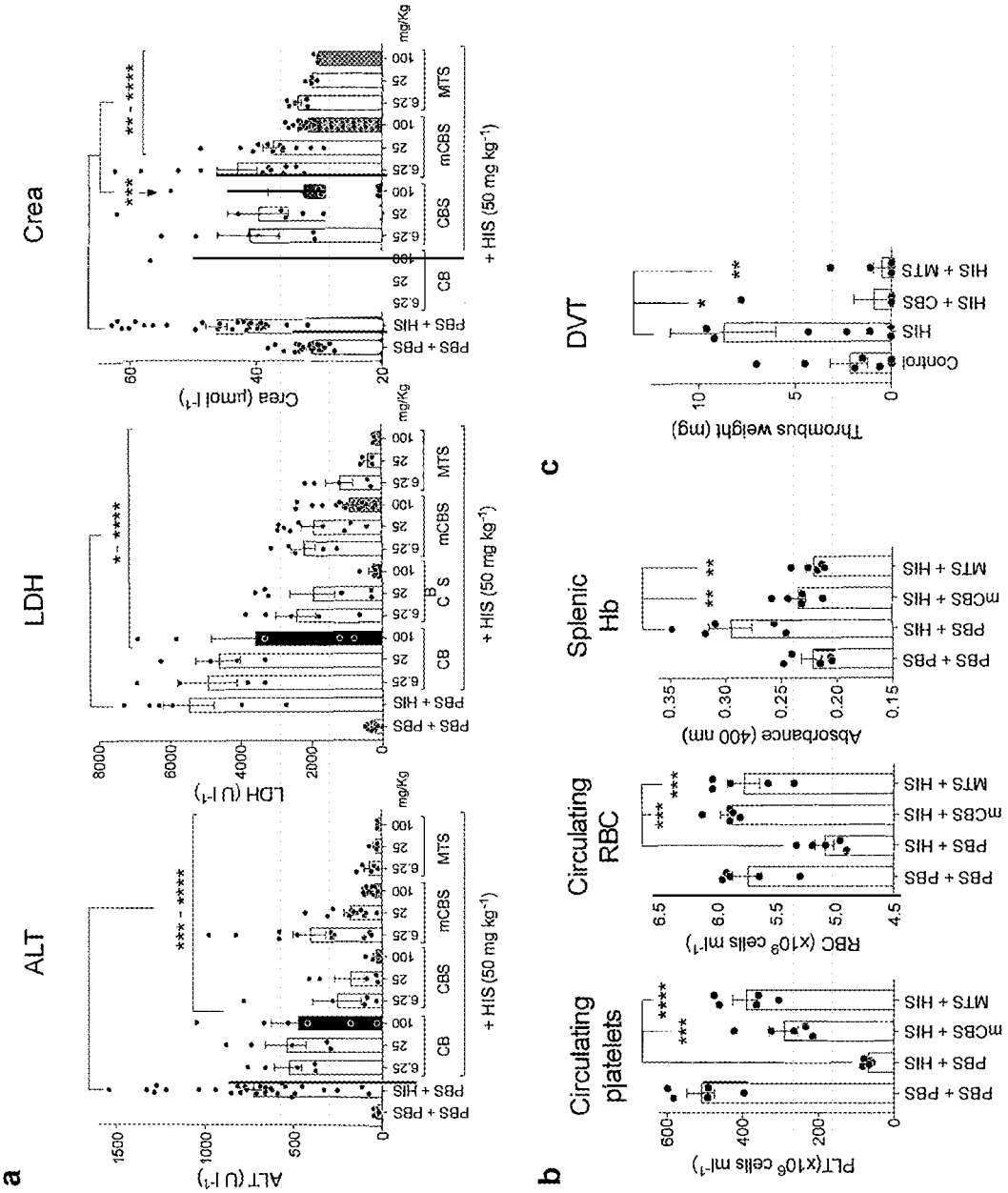
FIG. 6 In Vivo SPAs inhibit histone-induced tissue injury, thrombocytopenia, anaemia and DVT. a, Mice (n=5-28/group), injected i.p. with SPA doses (as indicated) 10 min prior to i.v. injection of histones (50 mg kg$^{-1}$), had their blood collected 4 h post-histones for assessment of liver (alanine aminotransferase, ALT), kidney (creatinine, Crea) and general tissue (lactate dehydrogenase, LDH) damage. Data pooled from 10 separate experiments, with n=5-28 mice/treatment. b, Mice (n=5/group), treated as above but receiving one SPA dosage (100 mg kg$^{-1}$), had their blood and spleens collected 10 min post-histones for assessment of circulating platelets and RBC and splenic haemoglobin (Hb). c, Impact of CBS and MTS on a mouse model of histone-induced DVT (n=7-10 mice/group). Data mean±s.e.m. *P≤0.05, P<0.01, *P<0.001, ****P<0.0001 (one way ANOVA with Dunnett's multiple comparisons test).

Example 5: Effect of CBS, mCBS and MTS on In Vivo Histone-Associated Pathologies The Inventors next assessed the ability of the CBS, mCBS and MTS to inhibit histone-mediated pathologies in vivo. Injection of histones intravenously into mice results in a sepsis-like syndrome involving liver damage, generalised tissue injury and kidney failure, as measured by circulating ALT, LDH and creatinine levels. Administration of CBS, mCBS and MTS protected animals from each of these tissue-specific pathologies in a concentration-dependent manner, with MTS being the most potent, CBS and mCBS being equally active and unsulfated CB being inactive (FIG. 6a). Systemic histones also induce thrombocytopenia and anaemia that was prevented by mCBS and MTS treatment (FIG. 6b). To examine whether CBS, mCBS and MTS influence the localised vascular effects of histones, a histone-mediated model of DVT (Brill, A. et al. von Willebrand factor-mediated platelet adhesion is critical for deep vein thrombosis in mouse models. *Blood* 117, 1400-1407(2011)) was established that revealed this to be almost totally inhibited by both CBS and MTS (FIG. 6c), consistent with both systemic and localised pathologies mediated by free histones being amenable to inhibition by CBS, mCBS and MTS.

Figure 7:
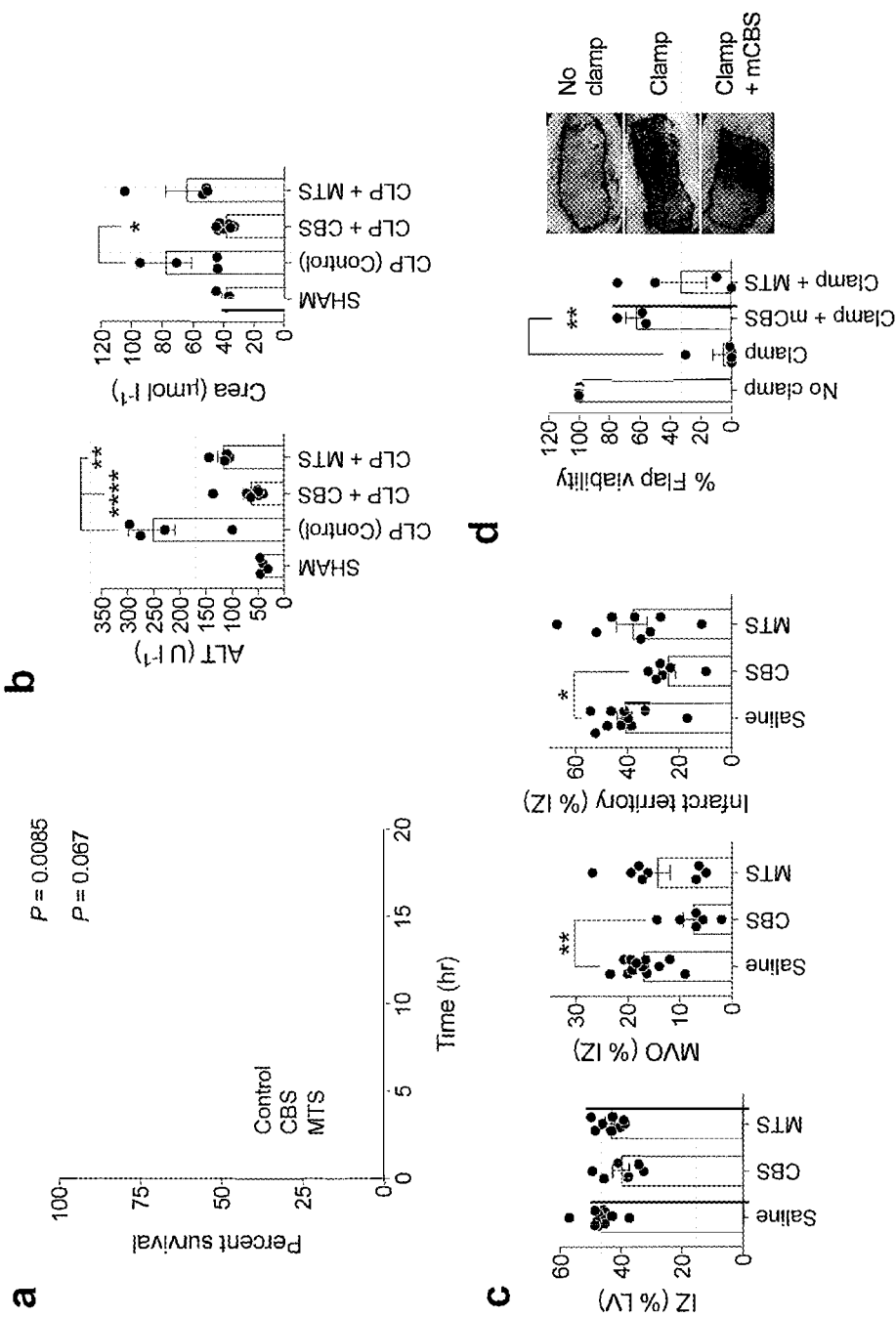
FIG. 7 SPAs inhibit a range of pathologies involving extracellular histones. a, Survival of rats (n=8/group) subjected to caecal ligation and puncture (CLP) and receiving saline (Control), CBS or MTS. P values obtained with Log rank (Mantel-Cox) test. b, Kidney and liver damage in CLP rats, as measured by ALT and creatinine blood levels. c, Effect of CBS and MTS (n=6-12/group) on cardiac IRI in rats, with ischemic zone (IZ) in left ventricle (LV), microvascular obstruction (MVO) and infarct territory being measured. d, Effect of mCBS and MTS on a skin flap model of IRI in mice (n=3-5/group), with representative photos shown. Statistical analysis of (b-d) as for FIG. 6.

The inventors next examined the efficacy of CBS, mCBS and MTS in a rat caecal ligation puncture (CLP) model of sepsis. There was no mortality in the CBS treatment group, an effect that was highly significant compared with PBS controls, and only one death occurred in the MTS group, which approached significance (FIG. 7a). Importantly, high ALT and creatinine levels detected in the untreated group, indicative of extensive liver and kidney damage, were not seen in the CBS treated animals but were only partially reduced in the MTS treatment group (FIG. 7b). This finding is somewhat paradoxical as in vitro and in vivo MTS was consistently a more potent neutraliser of DNA-free extracellular histones than mCBS/CBS.

To further investigate this paradox, CBS and MTS were tested for their efficacy in a rat cardiac ischemia reperfusion injury (IRI) model, previous studies having demonstrated that cardiac IRI is highly NET-dependent (Savchenko, A. S. et al. VWF-mediated leukocyte recruitment with chromatin decondensation by PAD4 increases myocardial ischemia/reperfusion injury in mice. *Blood* 123, 141-148, (2014); and Ge, L. et al. Neutrophil extracellular traps in ischemia-reperfusion injury-induced myocardial no-reflow: therapeutic potential of DNase-based reperfusion strategy. *Am J Physiol Heart Circ Physiol* 308, H500-509, (2015)). Remarkably, in this model MTS was totally ineffectual whereas CBS treatment significantly reduced the area of microvascular obstruction and myocardial necrosis in the ischemic zone by 50% (FIG. 7c). This unexpected finding was largely confirmed in a rat skin flap IRI model where mCBS consistently and significantly increased the viable area of the skin flap, whereas the results with MTS treatment were highly variable (FIG. 7d).

Figure 8:
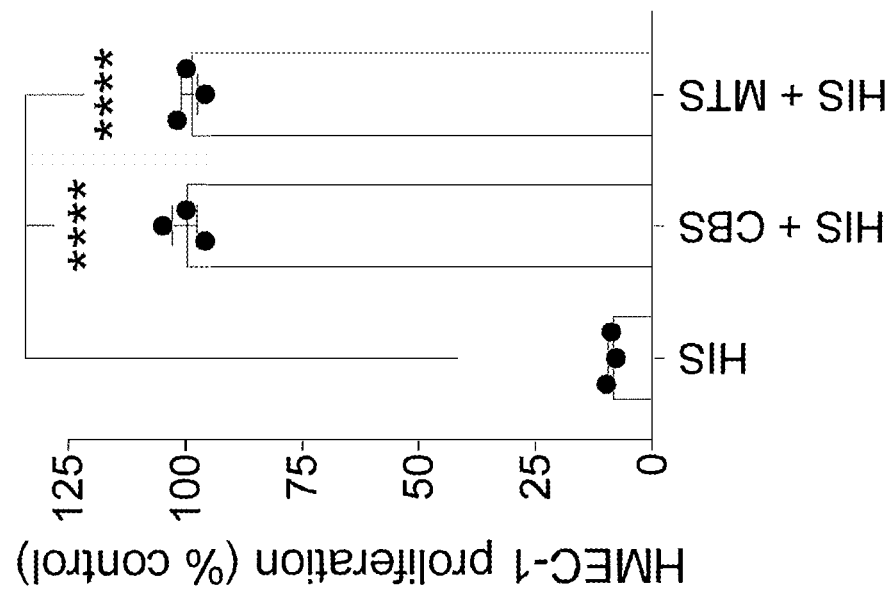
FIG. 8 HMEC-1 proliferation is a highly sensitive assay for both determining histone cytotoxicity and detecting inhibitors of this cytotoxicity. a, Sub-confluent HMEC-1 monolayers were exposed to increasing concentrations of histones for 3 h and then $^3$H-thymidine added and HMEC-1 proliferation measured by $^3$H-thymidine incorporation over the next 24 h, with HMEC-1 proliferation being inhibited, in a highly concentration-dependent manner, by histones. b, The SPAs mCBS and MTS (100 μg ml$^{-1}$) completely neutralized the anti-proliferative effect of histones (400 μg ml$^{-1}$) on HMEC-1 monolayers. Data are mean±s.e.m. (n=3 biological replicates). ****P<0.0001 (one way ANOVA with Dunnett's multiple comparisons test).
Figure 8:
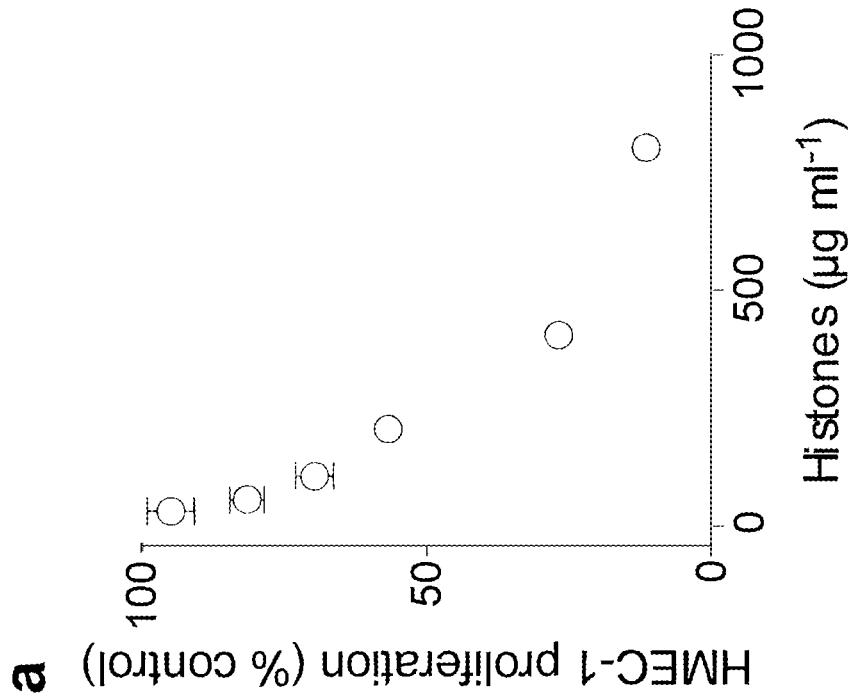
Figure 9:
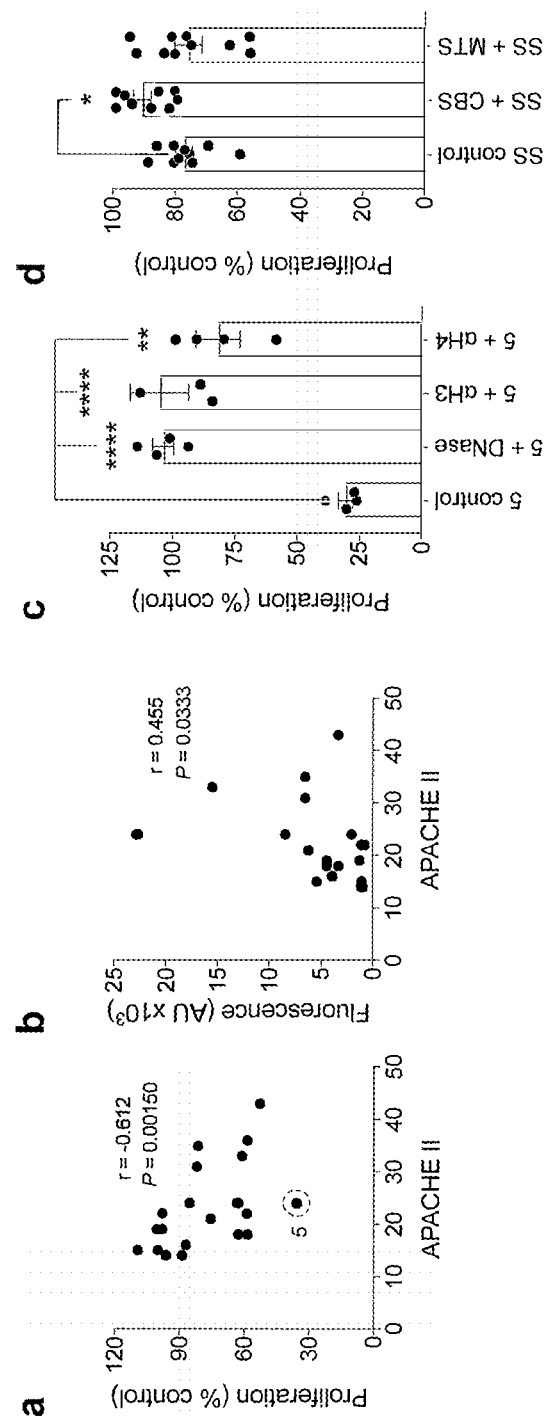
FIG. 9 Serum from sepsis patients is toxic for endothelial cells, an effect neutralized by DNase I, anti-histone antibodies and SPAs. a, Correlation (Spearman's r value) of APACHE II scores with anti-proliferative effect of sepsis patients sera on HMEC-1 (n=20 patients). b, Correlation of APACHE II scores with extracellular DNA content of sepsis patients sera. c, Effect of DNase I or pAbs against histone 3 (αH3) and histone 4 (αH4) (n=4 biological replicates/treatment) on anti-proliferative effect of serum from sepsis patient 5 (red circle, panel a). d, Ability of SPAs mCBS and MTS to neutralize the anti-proliferative effect of septic patient sera (SS)(n=10 patients). Statistical analysis as for FIG. 6.

Example 6: Comparison of the Ability of CBS, mCBS and MTS to Inhibit NETs in Sepsis Patient Sera Based on the in vivo efficacy data discussed above, we hypothesised that mCBS/CBS inhibit pathologies mediated by both DNA-free and NET-associated histones whereas MTS preferentially inhibits the damaging effects of DNA-free histones. Support for this interpretation was obtained using sera from sepsis patients that, we discovered, inhibited HMEC-1 proliferation, as measured by $^3$H-thymidine incorporation (FIG. 8a, b), at a level that highly correlated with their APACHE II scores (FIG. 9a). This correlation was stronger than that observed between APACHE II scores and circulating DNA levels (FIG. 9b). Further analysis of highly inhibitory serum from patient 5 revealed that this cytotoxic activity was DNase I sensitive and also was totally inhibited by polyclonal antibodies specific for histones 3 and 4 (FIG. 9c). Such data are consistent with NETs mediating the anti-proliferative effects of the septic patient's sera. Finally, the inventors found that CBS significantly overrode the anti-proliferative activity of the 10 most inhibitory septic patient sera, whereas MTS did not (FIG. 9d). Thus, these results are entirely consistent with MTS being a free histone inhibitor and mCBS/CBS inhibiting pathologies mediated by both DNA-free and NET-associated histones.

The invention claimed is:

1. A method of treating acute pancreatitis, wherein the method comprises administering to a subject in need thereof, a therapeutically effective amount of a polyanionic sulfated cellobioside compound having the general structure of

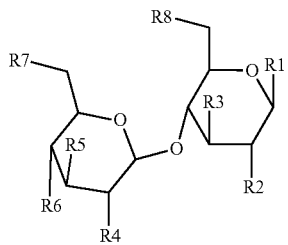

wherein R1 is methoxy, and wherein R2 to R8 are each selected from O-sulfate, or a pharmaceutically acceptable salt thereof.

2. The method according to claim 1, wherein the therapeutically effective amount of polyanionic sulfated cellobioside compound or the pharmaceutically acceptable salt thereof is sufficient to reduce, minimize or inhibit acute pancreatitis in the subject.

3. The method according to claim 1, wherein the therapeutically effective amount of the polyanionic sulfated cellobioside compound or the pharmaceutically acceptable salt thereof is sufficient to reduce, minimize or inhibit neutrophil extracellular trap (NETs) that (i) are cytotoxic towards the endothelium in the subject, or (ii) contribute to endothelial dysfunction in the subject, or (iii) initiate coagulation by activating platelets in the subject, or (iv) induce red cell fragility and resultant anaemia in the subject.

4. The method according to claim 1, comprising administering the therapeutically affective amount of the polyanionic sulfated cellobioside compound or the pharmaceutically acceptable salt thereof in a single dose.

5. The method according to claim 1, comprising administering the therapeutically affective amount of the polyanionic sulfated cellobioside compound or the pharmaceutically acceptable salt thereof, in multiple doses.

6. The method according to claim 1, wherein the polyanionic sulfated cellobioside compound is sulfated β-O-methyl cellobioside disaccharide, or sodium β-O-methyl cellobioside sulfate.

* * * * *